US009572557B2

(12) United States Patent
Gelbart et al.

(10) Patent No.: US 9,572,557 B2
(45) Date of Patent: Feb. 21, 2017

(54) METHOD AND DEVICE FOR CLOSING HOLES IN TISSUE

(71) Applicant: Kardium Inc., Vancouver (CA)

(72) Inventors: Daniel Gelbart, Vancouver (CA); Samuel Victor Lichtenstein, Vancouver (CA)

(73) Assignee: KARDIUM INC., Burnaby (CA)

(*) Notice: Subject to any disclaimer, the term of this patent is extended or adjusted under 35 U.S.C. 154(b) by 0 days.

(21) Appl. No.: 13/652,299

(22) Filed: Oct. 15, 2012

(65) Prior Publication Data

US 2013/0041405 A1    Feb. 14, 2013

Related U.S. Application Data

(60) Continuation of application No. 12/777,883, filed on May 11, 2010, now Pat. No. 8,337,524, which is a division of application No. 11/436,585, filed on May 19, 2006, now Pat. No. 7,749,249, which is a continuation-in-part of application No. 11/357,011, filed on Feb. 21, 2006, now abandoned.

(51) Int. Cl.
*A61B 17/08* (2006.01)
*A61B 17/00* (2006.01)
*A61B 17/22* (2006.01)

(52) U.S. Cl.
CPC .. *A61B 17/0057* (2013.01); *A61B 2017/00292* (2013.01); *A61B 2017/00575* (2013.01); *A61B 2017/00579* (2013.01); *A61B 2017/00592* (2013.01); *A61B 2017/00615* (2013.01); *A61B 2017/00623* (2013.01); *A61B 2017/00862* (2013.01); *A61B 2017/22061* (2013.01)

(58) Field of Classification Search
CPC ........... A61B 2017/00575; A61B 2017/00579; A61B 17/0057; A61B 17/08
USPC ......... 606/139, 142–143, 151–158, 213, 219
See application file for complete search history.

(56) References Cited

U.S. PATENT DOCUMENTS

| 566,521 A | 8/1896 | Leger |
| 3,132,438 A | 5/1964 | Ward et al. .................... 43/53.5 |
| 4,041,955 A | 8/1977 | Kelly et al. |
| 4,085,744 A | 4/1978 | Lewis et al. |
| 4,114,202 A | 9/1978 | Roy et al. .......................... 3/1.5 |
| 4,164,046 A | 8/1979 | Cooley ............................. 3/1.5 |

(Continued)

FOREIGN PATENT DOCUMENTS

| EP | 0723467 B1 | 4/2002 |
| EP | 2082690 A1 | 7/2009 |

(Continued)

OTHER PUBLICATIONS

Dahlgren et al., "Medical Device for Constricting Tissue or a Bodily Orifice, For Example a Mitral Valve," Office Action mailed Dec. 18, 2009, for U.S. Appl. No. 12/120,195, 9 pages.

(Continued)

*Primary Examiner* — Todd J Scherbel
*Assistant Examiner* — Son Dang
(74) *Attorney, Agent, or Firm* — Rossi, Kimms & McDowell LLP

(57) ABSTRACT

A device for closing holes in tissue is delivered via a catheter to the inside of a body lumen such as a heart. An elastic barbed clip is expanded, pulled into the tissue and released, pulling the tissue with it. The operation is fully reversible.

38 Claims, 9 Drawing Sheets

(56) References Cited

U.S. PATENT DOCUMENTS

| | | |
|---|---|---|
| 4,225,148 A | 9/1980 | Anderson |
| 4,240,441 A | 12/1980 | Khalil ........................ 128/692 |
| 4,261,342 A | 4/1981 | Aranguren Duo ............ 128/1 R |
| 4,263,680 A | 4/1981 | Reul et al. ........................ 3/1.5 |
| 4,273,128 A | 6/1981 | Lary |
| 4,411,266 A | 10/1983 | Cosman |
| 4,490,859 A | 1/1985 | Black et al. ...................... 3/1.5 |
| 4,527,554 A | 7/1985 | Klein |
| 4,543,090 A | 9/1985 | McCoy ........................... 604/95 |
| 4,699,147 A | 10/1987 | Chilson et al. |
| 4,770,187 A | 9/1988 | Lash et al. |
| 4,794,912 A | 1/1989 | Lia .................................. 128/4 |
| 4,850,957 A | 7/1989 | Summers ....................... 604/22 |
| 4,887,613 A | 12/1989 | Farr et al. |
| 4,890,602 A | 1/1990 | Hake ................................ 128/4 |
| 4,890,612 A | 1/1990 | Kensey ........................ 606/213 |
| 4,893,613 A | 1/1990 | Hake ................................ 128/4 |
| 4,895,166 A | 1/1990 | Farr et al. |
| 4,921,499 A | 5/1990 | Hoffman et al. .............. 623/16 |
| 4,942,788 A | 7/1990 | Farr et al. |
| 4,979,514 A | 12/1990 | Sekii et al. |
| 4,994,698 A | 2/1991 | Kliman et al. |
| 4,998,933 A | 3/1991 | Eggers et al. |
| 5,021,059 A | 6/1991 | Kensey et al. ............... 606/213 |
| 5,026,384 A | 6/1991 | Farr et al. |
| 5,039,894 A | 8/1991 | Teter et al. |
| 5,047,047 A | 9/1991 | Yoon .............................. 606/216 |
| 5,100,418 A | 3/1992 | Yoon et al. .................... 606/139 |
| 5,104,399 A | 4/1992 | Lazarus ........................... 623/1 |
| 5,122,137 A | 6/1992 | Lennox ........................... 606/40 |
| 5,127,902 A | 7/1992 | Fischell |
| 5,156,151 A | 10/1992 | Imran |
| 5,156,609 A | 10/1992 | Nakao et al. .................. 606/142 |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,192,314 A | 3/1993 | Daskalakis ........................ 623/3 |
| 5,201,316 A | 4/1993 | Pomeranz et al. |
| 5,228,442 A | 7/1993 | Imran |
| 5,242,386 A | 9/1993 | Holzer |
| 5,242,456 A | 9/1993 | Nash et al. |
| 5,245,987 A | 9/1993 | Redmond et al. |
| 5,258,000 A | 11/1993 | Gianturco ..................... 606/151 |
| 5,279,299 A | 1/1994 | Imran |
| 5,293,869 A | 3/1994 | Edwards et al. |
| 5,312,435 A | 5/1994 | Nash et al. .................... 606/213 |
| 5,312,439 A | 5/1994 | Loeb |
| 5,317,952 A | 6/1994 | Immega |
| 5,320,632 A | 6/1994 | Heidmueller ................. 606/144 |
| 5,341,807 A | 8/1994 | Nardella |
| 5,364,408 A | 11/1994 | Gordon ......................... 606/144 |
| 5,366,443 A | 11/1994 | Eggers et al. ................. 604/114 |
| 5,366,459 A | 11/1994 | Yoon .............................. 606/151 |
| 5,368,601 A | 11/1994 | Sauer et al. ................... 606/144 |
| 5,374,275 A | 12/1994 | Bradley et al. ............... 606/144 |
| 5,375,612 A | 12/1994 | Cottenceau et al. |
| 5,379,773 A | 1/1995 | Hornsby |
| 5,383,887 A | 1/1995 | Nadal |
| RE34,866 E | 2/1995 | Kensey et al. |
| 5,390,664 A | 2/1995 | Redmond et al. |
| 5,417,698 A | 5/1995 | Green et al. |
| 5,419,767 A | 5/1995 | Eggers et al. |
| 5,423,859 A | 6/1995 | Koyfman et al. |
| 5,450,860 A | 9/1995 | O'Connor ..................... 128/898 |
| 5,454,834 A | 10/1995 | Boebel et al. |
| 5,462,561 A | 10/1995 | Voda |
| 5,478,353 A | 12/1995 | Yoon .............................. 606/213 |
| 5,496,267 A | 3/1996 | Drasler et al. |
| 5,507,811 A | 4/1996 | Koike et al. |
| 5,531,760 A | 7/1996 | Alwafaie ...................... 606/216 |
| 5,557,967 A | 9/1996 | Renger |
| 5,558,091 A | 9/1996 | Acker et al. |
| 5,575,810 A | 11/1996 | Swanson et al. |
| 5,593,424 A | 1/1997 | Northrup III ................. 606/232 |
| 5,598,848 A | 2/1997 | Swanson et al. |
| 5,634,942 A | 6/1997 | Chevillon et al. |
| 5,645,566 A | 7/1997 | Brenneman et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,690,649 A | 11/1997 | Li |
| 5,697,285 A | 12/1997 | Nappi et al. |
| 5,713,896 A | 2/1998 | Nardella ......................... 606/50 |
| 5,716,397 A | 2/1998 | Myers ............................. 623/2 |
| 5,720,726 A | 2/1998 | Marcadis et al. .............. 604/96 |
| 5,728,114 A | 3/1998 | Evans et al. .................. 606/148 |
| 5,730,127 A | 3/1998 | Avitall |
| 5,752,965 A | 5/1998 | Francis et al. |
| 5,762,066 A | 6/1998 | Law et al. |
| 5,769,846 A | 6/1998 | Edwards et al. |
| 5,782,239 A | 7/1998 | Webster, Jr. |
| 5,782,861 A | 7/1998 | Cragg et al. .................. 606/216 |
| 5,782,879 A | 7/1998 | Rosborough et al. |
| 5,800,495 A | 9/1998 | Machek et al. ............... 607/116 |
| 5,824,066 A | 10/1998 | Gross ............................... 623/2 |
| 5,830,222 A | 11/1998 | Makower |
| 5,836,990 A | 11/1998 | Li .................................. 607/28 |
| 5,865,791 A | 2/1999 | Whayne et al. ................ 604/49 |
| 5,871,505 A | 2/1999 | Adams et al. |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,919,207 A | 7/1999 | Taheri ........................... 606/219 |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. ........ 600/16 |
| 5,964,782 A | 10/1999 | Lafontaine et al. .......... 606/213 |
| 5,971,994 A | 10/1999 | Fritzsch |
| 5,976,174 A | 11/1999 | Ruiz |
| 5,980,473 A | 11/1999 | Korakianitis et al. |
| 5,984,950 A | 11/1999 | Cragg et al. .................. 606/216 |
| 6,001,069 A | 12/1999 | Tachibana et al. .............. 601/2 |
| 6,024,096 A | 2/2000 | Buckberg ..................... 128/898 |
| 6,063,082 A | 5/2000 | DeVore et al. |
| 6,074,417 A | 6/2000 | Peredo ............................. 623/2 |
| 6,074,418 A | 6/2000 | Buchanan et al. |
| 6,104,944 A | 8/2000 | Martinelli ..................... 600/424 |
| 6,113,610 A | 9/2000 | Poncet .......................... 606/139 |
| 6,123,702 A | 9/2000 | Swanson et al. |
| 6,132,438 A | 10/2000 | Fleischman et al. ......... 606/139 |
| 6,138,043 A | 10/2000 | Avitall |
| 6,142,993 A | 11/2000 | Whayne et al. |
| 6,156,046 A | 12/2000 | Passafaro et al. |
| 6,183,496 B1 | 2/2001 | Urbanski |
| 6,203,554 B1 | 3/2001 | Roberts ........................ 606/144 |
| 6,210,432 B1 | 4/2001 | Solem et al. ................ 623/1.15 |
| 6,214,032 B1 | 4/2001 | Loeb et al. |
| 6,217,573 B1 | 4/2001 | Webster |
| 6,221,103 B1 | 4/2001 | Melvin ......................... 623/3.1 |
| 6,221,104 B1 | 4/2001 | Buckberg et al. ............ 623/3.1 |
| 6,231,561 B1 | 5/2001 | Frazier et al. |
| 6,241,747 B1 | 6/2001 | Ruff .............................. 606/216 |
| 6,248,124 B1 | 6/2001 | Pedros et al. ................. 606/213 |
| 6,258,258 B1 | 7/2001 | Sartori et al. ................. 208/263 |
| 6,261,309 B1 | 7/2001 | Urbanski |
| 6,266,550 B1 | 7/2001 | Selmon et al. |
| 6,287,321 B1 | 9/2001 | Jang .............................. 606/200 |
| 6,304,769 B1 | 10/2001 | Arenson et al. .............. 600/424 |
| 6,306,135 B1 | 10/2001 | Ellman et al. .................. 606/45 |
| 6,308,091 B1 | 10/2001 | Avitall |
| 6,332,864 B1 | 12/2001 | Schweich, Jr. et al. ........ 600/16 |
| 6,346,105 B1 | 2/2002 | Tu et al. ......................... 606/41 |
| 6,358,258 B1 | 3/2002 | Arcia et al. ................... 606/139 |
| 6,358,277 B1 | 3/2002 | Duran .......................... 623/2.12 |
| 6,360,749 B1 | 3/2002 | Jayaraman ................... 128/898 |
| 6,379,366 B1 | 4/2002 | Fleischman et al. ......... 606/139 |
| 6,383,151 B1 | 5/2002 | Diederich et al. |
| 6,389,311 B1 | 5/2002 | Whayne et al. |
| 6,391,048 B1 | 5/2002 | Ginn et al. .................... 606/213 |

(56) References Cited

U.S. PATENT DOCUMENTS

| | | | |
|---|---|---|---|
| 6,391,054 B2 | 5/2002 | Carpentier et al. ............ 623/2.37 |
| 6,402,680 B2 | 6/2002 | Mortier et al. ................. 600/16 |
| 6,402,781 B1 | 6/2002 | Langberg et al. ............ 623/2.36 |
| 6,406,420 B1 | 6/2002 | McCarthy et al. ............. 600/16 |
| 6,409,760 B1 | 6/2002 | Melvin ........................ 623/3.1 |
| 6,416,459 B1 | 7/2002 | Haindl .......................... 600/37 |
| 6,432,115 B1 | 8/2002 | Mollenauer et al. |
| 6,436,052 B1 | 8/2002 | Nikolic et al. ............... 600/529 |
| 6,450,171 B1 | 9/2002 | Buckberg et al. ............. 128/898 |
| 6,475,223 B1 | 11/2002 | Werp et al. .................... 606/108 |
| 6,485,409 B1 | 11/2002 | Voloshin et al. |
| 6,485,489 B2 | 11/2002 | Teirstein et al. ............... 606/41 |
| 6,506,210 B1 | 1/2003 | Kanner ......................... 606/213 |
| 6,514,249 B1 | 2/2003 | Maguire et al. |
| 6,529,756 B1 | 3/2003 | Phan et al. |
| 6,537,198 B1 | 3/2003 | Vidlund et al. ............... 600/16 |
| 6,537,314 B2 | 3/2003 | Langberg et al. ............ 623/2.36 |
| 6,540,670 B1 | 4/2003 | Hirata et al. ................. 600/152 |
| 6,551,312 B2 | 4/2003 | Zhang et al. ................... 606/41 |
| 6,569,160 B1 | 5/2003 | Goldin et al. .................. 606/41 |
| 6,569,198 B1 | 5/2003 | Wilson et al. ............... 623/2.37 |
| 6,575,971 B2 | 6/2003 | Hauck et al. .................. 606/52 |
| 6,582,447 B1 | 6/2003 | Patel et al. |
| 6,589,208 B2 | 7/2003 | Ewers et al. ................. 604/104 |
| 6,626,930 B1 | 9/2003 | Allen et al. .................. 606/213 |
| 6,632,238 B2 | 10/2003 | Ginn et al. .................... 606/213 |
| 6,662,034 B2 | 12/2003 | Segner et al. .................. 600/373 |
| 6,676,685 B2 | 1/2004 | Pedros et al. ................. 606/213 |
| 6,681,773 B2 | 1/2004 | Murphy et al. |
| 6,704,590 B2 | 3/2004 | Haldeman |
| 6,723,038 B1 | 4/2004 | Schroeder et al. ............ 600/16 |
| 6,726,704 B1 | 4/2004 | Loshakove et al. .......... 606/213 |
| 6,726,716 B2 | 4/2004 | Marquez ....................... 623/2.36 |
| 6,743,241 B2 | 6/2004 | Kerr .............................. 606/144 |
| 6,749,622 B2 | 6/2004 | McGuckin, Jr. et al. .... 606/213 |
| 6,752,810 B1 | 6/2004 | Gao et al. |
| 6,760,616 B2 | 7/2004 | Hoey et al. ................... 600/547 |
| 6,780,197 B2 | 8/2004 | Roe et al. ..................... 606/213 |
| 6,797,001 B2 | 9/2004 | Mathis et al. ................ 623/2.37 |
| 6,800,090 B2 | 10/2004 | Alferness et al. ............. 623/2.36 |
| 6,824,562 B2 | 11/2004 | Mathis et al. ................ 623/2.36 |
| 6,837,886 B2 | 1/2005 | Collins et al. |
| 6,840,957 B2 | 1/2005 | DiMatteo et al. ............ 623/1.24 |
| 6,852,076 B2 | 2/2005 | Nikolic et al. ................. 600/37 |
| 6,855,143 B2 | 2/2005 | Davison et al. ................ 606/41 |
| 6,881,218 B2 | 4/2005 | Beyer et al. |
| 6,890,353 B2 | 5/2005 | Cohn et al. ................... 623/2.37 |
| 6,892,091 B1 | 5/2005 | Ben-Haim et al. |
| 6,899,674 B2 | 5/2005 | Viebach et al. .............. 600/152 |
| 6,907,297 B2 | 6/2005 | Wellman et al. |
| 6,908,478 B2 | 6/2005 | Alferness et al. ........... 623/1.11 |
| 6,913,576 B2 | 7/2005 | Bowman |
| 6,918,903 B2 | 7/2005 | Bass |
| 6,926,669 B1 | 8/2005 | Stewart et al. |
| 6,941,171 B2 | 9/2005 | Mann et al. |
| 6,942,657 B2 | 9/2005 | Sinofsky et al. |
| 6,949,122 B2 | 9/2005 | Adams et al. ................ 623/2.36 |
| 6,960,229 B2 | 11/2005 | Mathis et al. ................ 623/2.36 |
| 6,986,775 B2 | 1/2006 | Morales et al. ................ 606/139 |
| 6,989,010 B2 | 1/2006 | Francischelli et al. |
| 6,989,028 B2 | 1/2006 | Lashinski et al. ............ 623/2.37 |
| 6,991,649 B2 | 1/2006 | Sievers ......................... 623/2.23 |
| 6,994,093 B2 | 2/2006 | Murphy et al. ................ 128/898 |
| 6,997,951 B2 | 2/2006 | Solem et al. ................. 623/2.37 |
| 7,001,383 B2 | 2/2006 | Keidar |
| 7,025,776 B1 | 4/2006 | Houser et al. ................. 606/213 |
| 7,050,848 B2 | 5/2006 | Hoey et al. ................... 600/547 |
| 7,052,487 B2 | 5/2006 | Cohn et al. ................... 604/509 |
| 7,068,867 B2 | 6/2006 | Adoram et al. |
| 7,101,395 B2 | 9/2006 | Tremulis et al. ............ 623/2.11 |
| 7,141,019 B2 | 11/2006 | Pearlman |
| 7,144,363 B2 | 12/2006 | Pai et al. ........................ 600/16 |
| 7,160,322 B2 | 1/2007 | Gabbay ........................ 623/2.36 |
| 7,166,127 B2 | 1/2007 | Spence et al. ................ 623/2.37 |
| 7,177,677 B2 | 2/2007 | Kaula et al. .................. 600/546 |
| 7,186,210 B2 | 3/2007 | Feld et al. ....................... 600/16 |
| 7,187,964 B2 | 3/2007 | Khoury |
| 7,189,202 B2 | 3/2007 | Lau et al. ........................ 600/37 |
| 7,276,044 B2 | 10/2007 | Ferry et al. |
| 7,279,007 B2 | 10/2007 | Nikolic et al. ............. 623/11.11 |
| 7,280,863 B2 | 10/2007 | Shachar |
| 7,300,435 B2 | 11/2007 | Wham et al. ................... 606/34 |
| 7,303,526 B2 | 12/2007 | Sharkey et al. ................ 600/37 |
| 7,320,665 B2 | 1/2008 | Vijay |
| 7,335,196 B2 | 2/2008 | Swanson et al. |
| 7,374,530 B2 | 5/2008 | Schaller ........................ 600/16 |
| 7,399,271 B2 | 7/2008 | Khairkhahan et al. ......... 600/16 |
| 7,413,568 B2 | 8/2008 | Swanson et al. |
| 7,431,726 B2 | 10/2008 | Spence et al. ................ 606/151 |
| 7,452,325 B2 | 11/2008 | Schaller ........................ 600/37 |
| 7,452,375 B2 | 11/2008 | Mathis et al. |
| 7,507,252 B2 | 3/2009 | Lashinski et al. ............ 623/2.37 |
| 7,513,867 B2 | 4/2009 | Lichtenstein |
| 7,582,051 B2 | 9/2009 | Khairkhahan et al. ......... 600/16 |
| 7,611,534 B2 | 11/2009 | Kapadia et al. ............. 623/2.17 |
| 7,674,276 B2 | 3/2010 | Stone et al. |
| 7,704,277 B2 | 4/2010 | Zakay et al. ................. 623/2.12 |
| 7,736,388 B2 | 6/2010 | Goldfarb et al. |
| 7,738,967 B2 | 6/2010 | Salo |
| 7,749,249 B2 | 7/2010 | Gelbart et al. ............... 606/216 |
| 7,837,610 B2 | 11/2010 | Lichtenstein et al. |
| 7,869,854 B2 | 1/2011 | Shachar et al. |
| 7,873,402 B2 | 1/2011 | Shachar |
| 7,887,482 B2 | 2/2011 | Hamada |
| 8,027,714 B2 | 9/2011 | Shachar |
| 8,128,644 B2 | 3/2012 | Carley et al. |
| 8,150,499 B2 | 4/2012 | Gelbart et al. |
| 8,337,524 B2 | 12/2012 | Gelbart et al. |
| 8,449,605 B2 | 5/2013 | Lichtenstein et al. |
| 8,532,746 B2 | 9/2013 | Gelbart et al. |
| 8,672,998 B2 | 3/2014 | Lichtenstein et al. |
| 2001/0003158 A1 | 6/2001 | Kensey et al. ................ 606/213 |
| 2001/0005787 A1 | 6/2001 | Oz et al. ...................... 606/142 |
| 2001/0018611 A1 | 8/2001 | Solem et al. ................. 623/2.37 |
| 2001/0020126 A1 | 9/2001 | Swanson et al. ............. 600/407 |
| 2001/0041915 A1 | 11/2001 | Roue et al. |
| 2001/0044568 A1 | 11/2001 | Langberg et al. .............. 600/37 |
| 2002/0002329 A1 | 1/2002 | Avitall |
| 2002/0013621 A1 | 1/2002 | Stobie et al. |
| 2002/0016628 A1 | 2/2002 | Langberg et al. ............ 623/2.36 |
| 2002/0026092 A1 | 2/2002 | Buckberg et al. ............. 600/37 |
| 2002/0055775 A1 | 5/2002 | Carpentier et al. ......... 623/2.17 |
| 2002/0082621 A1 | 6/2002 | Schurr et al. ................ 606/151 |
| 2002/0087156 A1 | 7/2002 | Maguire et al. |
| 2002/0087173 A1 | 7/2002 | Alferness et al. ............ 606/151 |
| 2002/0107478 A1 | 8/2002 | Wendlandt |
| 2002/0107511 A1 | 8/2002 | Collins et al. |
| 2002/0107530 A1 | 8/2002 | Sauer et al. |
| 2002/0111647 A1 | 8/2002 | Khairkhahan et al. |
| 2002/0115944 A1 | 8/2002 | Mendes et al. ............... 600/594 |
| 2002/0133143 A1 | 9/2002 | Murphy et al. |
| 2002/0161394 A1 | 10/2002 | Macoviak et al. ............ 606/200 |
| 2002/0161406 A1 | 10/2002 | Silvian |
| 2002/0169359 A1 | 11/2002 | McCarthy et al. ............. 600/16 |
| 2002/0169360 A1 | 11/2002 | Taylor et al. .................... 600/37 |
| 2002/0169504 A1 | 11/2002 | Alferness et al. ........... 623/2.36 |
| 2002/0177782 A1 | 11/2002 | Penner |
| 2002/0183836 A1 | 12/2002 | Liddicoat et al. ............ 623/2.11 |
| 2002/0183841 A1 | 12/2002 | Cohn et al. ................... 623/2.36 |
| 2002/0188170 A1 | 12/2002 | Santamore et al. ............ 600/37 |
| 2002/0198603 A1 | 12/2002 | Buckberg et al. ......... 623/23.71 |
| 2003/0018358 A1 | 1/2003 | Saadat |
| 2003/0023241 A1 | 1/2003 | Drewry et al. |
| 2003/0028202 A1 | 2/2003 | Sancoff et al. |
| 2003/0036755 A1* | 2/2003 | Ginn ............................. 606/41 |
| 2003/0045896 A1 | 3/2003 | Murphy et al. ................ 606/191 |
| 2003/0050682 A1 | 3/2003 | Sharkey et al. ............... 607/126 |
| 2003/0050685 A1 | 3/2003 | Nikolic et al. ............... 623/1.11 |
| 2003/0050693 A1 | 3/2003 | Quijano et al. |
| 2003/0069570 A1 | 4/2003 | Witzel et al. .................. 606/28 |
| 2003/0069593 A1 | 4/2003 | Tremulis et al. |
| 2003/0069636 A1 | 4/2003 | Solem et al. ................. 623/2.37 |
| 2003/0078465 A1 | 4/2003 | Pai et al. ........................ 600/16 |
| 2003/0078652 A1 | 4/2003 | Sutherland .................... 623/2.12 |

(56) References Cited

U.S. PATENT DOCUMENTS

| Publication No. | Date | Name | Ref |
|---|---|---|---|
| 2003/0078671 A1 | 4/2003 | Lesniak et al. | 623/23.64 |
| 2003/0083742 A1 | 5/2003 | Spence et al. | |
| 2003/0105384 A1 | 6/2003 | Sharkey et al. | 600/16 |
| 2003/0105520 A1 | 6/2003 | Alferness et al. | 623/2.36 |
| 2003/0109770 A1 | 6/2003 | Sharkey et al. | 600/16 |
| 2003/0124480 A1 | 7/2003 | Peacock | |
| 2003/0149333 A1 | 8/2003 | Alferness | 600/16 |
| 2003/0158570 A1 | 8/2003 | Ferrazzi | |
| 2003/0163191 A1 | 8/2003 | Nikolic et al. | 623/1.11 |
| 2003/0167055 A1 | 9/2003 | Kolata et al. | |
| 2003/0181819 A1 | 9/2003 | Desai | |
| 2003/0208210 A1 | 11/2003 | Dreyfuss et al. | |
| 2003/0212453 A1 | 11/2003 | Mathis et al. | |
| 2003/0220667 A1 | 11/2003 | van der Burg et al. | 606/200 |
| 2003/0229395 A1 | 12/2003 | Cox | 623/2.36 |
| 2004/0002626 A1 | 1/2004 | Feld et al. | 600/37 |
| 2004/0054279 A1 | 3/2004 | Hanley | 600/424 |
| 2004/0122516 A1 | 6/2004 | Fogarty et al. | |
| 2004/0127916 A1 | 7/2004 | Bolduc et al. | |
| 2004/0133220 A1 | 7/2004 | Lashinski et al. | |
| 2004/0133273 A1 | 7/2004 | Cox | 623/2.11 |
| 2004/0138529 A1 | 7/2004 | Wiltshire et al. | 600/144 |
| 2004/0138744 A1 | 7/2004 | Lashinski et al. | 623/2.36 |
| 2004/0138745 A1 | 7/2004 | Macoviak et al. | 623/2.36 |
| 2004/0153146 A1 | 8/2004 | Lashinski et al. | 623/2.36 |
| 2004/0153147 A1 | 8/2004 | Mathis | |
| 2004/0158321 A1 | 8/2004 | Reuter et al. | 623/2.36 |
| 2004/0176797 A1 | 9/2004 | Opolski | |
| 2004/0176800 A1 | 9/2004 | Paraschac et al. | |
| 2004/0186566 A1 | 9/2004 | Hindrichs et al. | 623/2.37 |
| 2004/0193187 A1 | 9/2004 | Boehringer et al. | |
| 2004/0215232 A1 | 10/2004 | Belhe et al. | 606/213 |
| 2004/0220593 A1 | 11/2004 | Greenhalgh | |
| 2004/0236419 A1 | 11/2004 | Milo | |
| 2004/0243170 A1 | 12/2004 | Suresh et al. | 606/198 |
| 2004/0249408 A1 | 12/2004 | Murphy et al. | 606/198 |
| 2004/0249453 A1 | 12/2004 | Cartledge et al. | 623/2.37 |
| 2004/0260390 A1 | 12/2004 | Sarac et al. | 623/1.24 |
| 2004/0260393 A1 | 12/2004 | Rahdert et al. | 623/2.36 |
| 2004/0267191 A1 | 12/2004 | Gifford, III et al. | |
| 2004/0267358 A1 | 12/2004 | Reitan | 623/2.37 |
| 2005/0004668 A1 | 1/2005 | Aklog et al. | 623/2.36 |
| 2005/0015109 A1 | 1/2005 | Lichtenstein | 606/200 |
| 2005/0038509 A1 | 2/2005 | Ashe | 623/2.36 |
| 2005/0054938 A1 | 3/2005 | Wehman et al. | 600/483 |
| 2005/0055089 A1 | 3/2005 | Macoviak et al. | 623/2.37 |
| 2005/0060030 A1 | 3/2005 | Lashinski et al. | 623/2.37 |
| 2005/0064665 A1 | 3/2005 | Han | 438/286 |
| 2005/0065420 A1 | 3/2005 | Collins et al. | |
| 2005/0065504 A1 | 3/2005 | Melsky et al. | |
| 2005/0075727 A1 | 4/2005 | Wheatley | 623/2.17 |
| 2005/0080402 A1 | 4/2005 | Santamore et al. | 606/1 |
| 2005/0090840 A1 | 4/2005 | Gerbino et al. | |
| 2005/0096047 A1 | 5/2005 | Haberman et al. | 455/432.3 |
| 2005/0096498 A1 | 5/2005 | Hauser et al. | |
| 2005/0096589 A1 | 5/2005 | Shachar | |
| 2005/0096647 A1 | 5/2005 | Steinke et al. | |
| 2005/0107723 A1 | 5/2005 | Wehman et al. | 600/595 |
| 2005/0107871 A1 | 5/2005 | Realyvasquez et al. | 623/2.11 |
| 2005/0125030 A1 | 6/2005 | Forsberg et al. | 606/213 |
| 2005/0131441 A1 | 6/2005 | Iio et al. | |
| 2005/0137659 A1 | 6/2005 | Garabedian et al. | |
| 2005/0137689 A1 | 6/2005 | Salahieh et al. | 623/2.11 |
| 2005/0137695 A1 | 6/2005 | Salahieh et al. | |
| 2005/0137700 A1 | 6/2005 | Spence et al. | 623/2.36 |
| 2005/0143809 A1 | 6/2005 | Salahieh et al. | 623/2.11 |
| 2005/0148892 A1 | 7/2005 | Desai | |
| 2005/0149014 A1 | 7/2005 | Hauck et al. | 606/41 |
| 2005/0149114 A1 | 7/2005 | Cartledge et al. | 606/213 |
| 2005/0154252 A1 | 7/2005 | Sharkey et al. | 600/37 |
| 2005/0177180 A1 | 8/2005 | Kaganov et al. | 606/151 |
| 2005/0177227 A1 | 8/2005 | Heim et al. | 623/2.12 |
| 2005/0182365 A1 | 8/2005 | Hennemann et al. | 604/113 |
| 2005/0187620 A1 | 8/2005 | Pai et al. | 623/2.37 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0197716 A1 | 9/2005 | Sharkey et al. | 623/23.67 |
| 2005/0203558 A1 | 9/2005 | Maschke | |
| 2005/0209636 A1 | 9/2005 | Widomski et al. | 606/213 |
| 2005/0216052 A1 | 9/2005 | Mazzocchi et al. | 606/200 |
| 2005/0216054 A1 | 9/2005 | Widomski et al. | 606/213 |
| 2005/0240249 A1 | 10/2005 | Tu et al. | 607/96 |
| 2005/0251116 A1 | 11/2005 | Steinke et al. | 606/8 |
| 2005/0251132 A1 | 11/2005 | Oral et al. | |
| 2005/0256521 A1 | 11/2005 | Kozel | |
| 2005/0267573 A9 | 12/2005 | Macoviak et al. | 623/2.36 |
| 2005/0267574 A1 | 12/2005 | Cohn et al. | 623/2.36 |
| 2005/0273138 A1 | 12/2005 | To et al. | |
| 2006/0004424 A1 | 1/2006 | Loeb et al. | |
| 2006/0009755 A1 | 1/2006 | Sra | |
| 2006/0009756 A1 | 1/2006 | Francischelli et al. | |
| 2006/0014998 A1 | 1/2006 | Sharkey et al. | 600/16 |
| 2006/0015002 A1 | 1/2006 | Moaddeb et al. | 600/37 |
| 2006/0015003 A1 | 1/2006 | Moaddes et al. | 600/37 |
| 2006/0015038 A1 | 1/2006 | Weymarn-Scharli | 600/585 |
| 2006/0015096 A1 | 1/2006 | Hauck et al. | |
| 2006/0025784 A1 | 2/2006 | Starksen et al. | |
| 2006/0025800 A1 | 2/2006 | Suresh | 606/198 |
| 2006/0030881 A1 | 2/2006 | Sharkey et al. | 606/213 |
| 2006/0052867 A1* | 3/2006 | Revuelta et al. | 623/2.18 |
| 2006/0058871 A1 | 3/2006 | Zakay et al. | 623/2.18 |
| 2006/0085049 A1 | 4/2006 | Cory et al. | |
| 2006/0135968 A1 | 6/2006 | Schaller | 606/144 |
| 2006/0135970 A1 | 6/2006 | Schaller | 606/152 |
| 2006/0173536 A1 | 8/2006 | Mathis et al. | 623/2.11 |
| 2006/0184242 A1 | 8/2006 | Lichtenstein | 623/2.37 |
| 2006/0199995 A1 | 9/2006 | Vijay | 600/37 |
| 2006/0229491 A1 | 10/2006 | Sharkey et al. | 600/37 |
| 2006/0235286 A1 | 10/2006 | Stone et al. | 600/381 |
| 2006/0235314 A1 | 10/2006 | Migliuolo et al. | |
| 2006/0241334 A1 | 10/2006 | Dubi et al. | 600/16 |
| 2006/0241745 A1 | 10/2006 | Solem | 623/2.18 |
| 2006/0264980 A1 | 11/2006 | Khairkhahan et al. | 606/153 |
| 2006/0276683 A1 | 12/2006 | Feld et al. | 600/16 |
| 2006/0281965 A1 | 12/2006 | Khairkhahan et al. | 600/37 |
| 2006/0293698 A1 | 12/2006 | Douk | 606/142 |
| 2006/0293725 A1 | 12/2006 | Rubinsky et al. | |
| 2007/0010817 A1 | 1/2007 | de Coninck | |
| 2007/0016006 A1 | 1/2007 | Shachar | |
| 2007/0016068 A1 | 1/2007 | Grunwald et al. | 600/468 |
| 2007/0016288 A1 | 1/2007 | Gurskis et al. | |
| 2007/0027533 A1 | 2/2007 | Douk | 623/2.11 |
| 2007/0038208 A1 | 2/2007 | Kefer | |
| 2007/0050019 A1 | 3/2007 | Hyde | |
| 2007/0060895 A1 | 3/2007 | Sibbitt et al. | |
| 2007/0083076 A1 | 4/2007 | Lichtenstein | |
| 2007/0088362 A1 | 4/2007 | Bonutti et al. | |
| 2007/0115390 A1 | 5/2007 | Makara et al. | |
| 2007/0118151 A1 | 5/2007 | Davidson | |
| 2007/0118215 A1 | 5/2007 | Moaddeb | 623/2.37 |
| 2007/0129717 A1 | 6/2007 | Brown, III et al. | |
| 2007/0135826 A1 | 6/2007 | Zaver et al. | |
| 2007/0135913 A1 | 6/2007 | Moaddeb et al. | |
| 2007/0156233 A1 | 7/2007 | Kapadia et al. | 623/2.11 |
| 2007/0161846 A1 | 7/2007 | Nikolic et al. | 600/16 |
| 2007/0185571 A1 | 8/2007 | Kapadia et al. | 623/2.11 |
| 2007/0198057 A1 | 8/2007 | Gelbart et al. | |
| 2007/0198058 A1 | 8/2007 | Gelbart et al. | 606/213 |
| 2007/0213578 A1 | 9/2007 | Khairkhahan et al. | 600/16 |
| 2007/0213815 A1 | 9/2007 | Khairkhahan et al. | 623/3.1 |
| 2007/0219460 A1 | 9/2007 | Goldenberg | 600/566 |
| 2007/0225736 A1 | 9/2007 | Zeiner et al. | |
| 2007/0249999 A1 | 10/2007 | Sklar et al. | |
| 2007/0250160 A1 | 10/2007 | Rafiee | 623/2.11 |
| 2007/0270681 A1 | 11/2007 | Phillips et al. | |
| 2007/0270688 A1 | 11/2007 | Gelbart et al. | 600/427 |
| 2007/0270943 A1 | 11/2007 | Solem et al. | 623/2.11 |
| 2007/0299343 A1 | 12/2007 | Waters | |
| 2008/0004534 A1 | 1/2008 | Gelbart et al. | |
| 2008/0004643 A1 | 1/2008 | To et al. | 606/159 |
| 2008/0004697 A1 | 1/2008 | Lichtenstein et al. | 623/2.11 |
| 2008/0033541 A1 | 2/2008 | Gelbart et al. | 623/2.11 |
| 2008/0045778 A1 | 2/2008 | Lichtenstein et al. | 600/16 |

(56) References Cited

U.S. PATENT DOCUMENTS

| | | | |
|---|---|---|---|
| 2008/0051802 A1 | 2/2008 | Schostek et al. | |
| 2008/0071298 A1 | 3/2008 | Khairkhahan et al. | 606/151 |
| 2008/0086164 A1 | 4/2008 | Rowe | 606/191 |
| 2008/0132915 A1 | 6/2008 | Buckman et al. | |
| 2008/0133002 A1 | 6/2008 | Gelbart et al. | 623/2.1 |
| 2008/0140188 A1 | 6/2008 | Rahdert et al. | 623/2.1 |
| 2008/0177300 A1 | 7/2008 | Mas et al. | |
| 2008/0228266 A1 | 9/2008 | McNamara et al. | |
| 2008/0262609 A1 | 10/2008 | Gross et al. | |
| 2008/0269785 A1 | 10/2008 | Lampropoulos et al. | |
| 2008/0275477 A1 | 11/2008 | Sterrett et al. | |
| 2008/0288060 A1 | 11/2008 | Kaye et al. | |
| 2008/0312713 A1 | 12/2008 | Wilfley et al. | |
| 2009/0076597 A1 | 3/2009 | Dahlgren et al. | 623/2.1 |
| 2009/0131930 A1 | 5/2009 | Gelbart et al. | |
| 2009/0157058 A1 | 6/2009 | Ferren et al. | |
| 2009/0192441 A1 | 7/2009 | Gelbart et al. | |
| 2009/0192527 A1 | 7/2009 | Messas | |
| 2009/0192539 A1 | 7/2009 | Lichtenstein | |
| 2009/0204180 A1 | 8/2009 | Gelbart | |
| 2009/0287304 A1 | 11/2009 | Dahlgren et al. | 623/2.37 |
| 2010/0087836 A1 | 4/2010 | Jaramillo et al. | |
| 2010/0087837 A1 | 4/2010 | Jaramillo et al. | |
| 2010/0161047 A1 | 6/2010 | Cabiri | |
| 2010/0222789 A1 | 9/2010 | Gelbart et al. | 606/142 |
| 2011/0022166 A1 | 1/2011 | Dahlgren et al. | |
| 2011/0082538 A1 | 4/2011 | Dahlgren et al. | |
| 2011/0087203 A1 | 4/2011 | Lichtenstein et al. | |
| 2011/0087227 A1 | 4/2011 | Mazur et al. | |
| 2011/0125172 A1 | 5/2011 | Gelbart et al. | |
| 2011/0172658 A1 | 7/2011 | Gelbart et al. | |
| 2011/0301618 A1 | 12/2011 | Lichtenstein | |
| 2012/0083806 A1 | 4/2012 | Goertzen | |
| 2012/0158016 A1 | 6/2012 | Gelbart et al. | |
| 2012/0245604 A1 | 9/2012 | Tegzes | |
| 2013/0041405 A1 | 2/2013 | Gelbart et al. | |
| 2013/0238089 A1 | 9/2013 | Lichtenstein et al. | |
| 2013/0345797 A1 | 12/2013 | Dahlgren et al. | |
| 2014/0135913 A1 | 5/2014 | Lichtenstein et al. | |

FOREIGN PATENT DOCUMENTS

| | | |
|---|---|---|
| WO | 90/15582 | 12/1990 |
| WO | 95/10320 A1 | 4/1995 |
| WO | 01/78625 | 10/2001 |
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/007031 A2 | 1/2005 |
| WO | 2005/046520 | 5/2005 |
| WO | 2005/070330 | 8/2005 |
| WO | 2005/102181 | 11/2005 |
| WO | 2006/017809 | 2/2006 |
| WO | 2006/105121 A2 | 10/2006 |
| WO | 2006/135747 | 12/2006 |
| WO | 2006/135749 | 12/2006 |
| WO | 2007/021647 | 2/2007 |
| WO | 2007/115390 | 10/2007 |
| WO | 2008/002606 A2 | 1/2008 |
| WO | 2009/065042 A2 | 5/2009 |

OTHER PUBLICATIONS

Dahlgren et al., "Medical Device for Constricting Tissue or a Bodily Orifice, For Example a Mitral Valve," Amendment filed Apr. 13, 2010, for U.S. Appl. No. 12/120,195, 22 pages.

Dahlgren et al., "Medical Device for Constricting Tissue or a Bodily Orifice, For Example a Mitral Valve," Office Action mailed Jul. 7, 2010, for U.S. Appl. No. 12/120,195, 14 pages.

Dahlgren et al., "Medical Device for Constricting Tissue or a Bodily Orifice, for Example a Mitral Valve," Preliminary Amendment filed Oct. 6, 2010 for U.S. Appl. No. 12/899,407, 8 pages.

Lichtenstein et al, "Method for Anchoring a Mitral Valve," Amendment filed Mar. 26, 2010, for U.S. Appl. No. 11/475,978, 26 pages.

Lichtenstein et al., "System for Improving Diastolic Dysfunction," Office Action mailed Dec. 24, 2008 for U.S. Appl. No. 11/497,309, 8 pages.

Lichtenstein et al., "System for Improving Diastolic Dysfunction," Amendment filed Apr. 22, 2009 for U.S. Appl. No. 11/497,309, 23 pages.

Lichtenstein et al., "System for Improving Diastolic Dysfunction," Office Action mailed Aug. 5, 2009 for U.S. Appl. No. 11/497,309, 10 pages.

Lichtenstein et al., "System for Improving Diastolic Dysfunction," Amendment filed Oct. 23, 2009 for U.S. Appl. No. 11/497,309, 9 pages.

Lichtenstein et al., "System for Improving Diastolic Dysfunction," Office Action mailed Jan. 20, 2010 for U.S. Appl. No. 11/497,309, 10 pages.

Lichtenstein et al., "System for Improving Diastolic Dysfunction," Amendment filed Apr. 7, 2010 for U.S. Appl. No. 11/497,309, 8 pages.

Gelbart et al., "Artificial Valve," Office Action mailed May 7, 2010 for U.S. Appl. No. 11/497,306, 12 pages.

Gelbart et al., "Artificial Valve," Amendment filed Jan. 29, 2010 for U.S. Appl. No. 11/497,306, 22 pages.

Athanasuleas et al., "Surgical Anterior Ventricular Restoration for Ischemic Cardiomyopathy," *Operative Techniques in Thoracic and Cardiovascular Surgery* 7(2):66-75, May 2002.

Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.

Cardiac Implants, URL=http://nmtmedical.com/products/ci/index. htm, download date May 13, 2006, 1 page.

Cooley, "Ventricular Aneurysms and Akinesis," *Cleveland Clinic Quarterly* 45(1):130-132, 1978.

Dahlgren et al., "Medical Device, Kit and Method for Constricting Tissue or a Bodily Orifice, For Example a Mitral Valve," U.S. Appl. No. 61/278,232, filed Oct. 1, 2009, 215 pages.

David et al., "Postinfarction Ventricular Septal Rupture: Repair by Endocardial Patch with Infarct Exclusion," *Journal of Thoracic and Card Surgery* 110(5):1315-1322, 1995.

Dor et al., "Left Ventricular Aneurysm: A New Surgical Approach," *Thoracic Cardiovascular Surgery* 37:11-19, 1989.

Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.

Dor, "Left Ventricular Aneurysms: The Endoventricular Circular Patch Plasty," *Seminars in Thoracic and Cardiovascular Surgery* 9(2):123-130, Apr. 1997.

Gelbart et al., "Automatic Atherectomy System," U.S. Appl. No. 11/436,584, filed May 19, 2006, 16 pages.

Gelbart et al., "Method and Device for Closing Holes in Tissue," U.S. Appl. No. 11/436,585, filed May 19, 2006, 12 pages.

Gelbart et al., "Method and Device for Closing Holes in Tissue," Office Action mailed Sep. 4, 2008, for U.S. Appl. No. 11/436,585, 8 pages.

Gelbart et al., "Method and Device for Closing Holes in Tissue," Amendment filed Sep. 22, 2008, for U.S. Appl. No. 11/436,585, 3 pages.

Gelbart et al., "Method and Device for Closing Holes in Tissue," Office Action mailed Jan. 2, 2009, for U.S. Appl. No. 11/436,585, 11 pages.

Gelbart et al., "Method and Device for Closing Holes in Tissue," Amendment filed Jan. 30, 2009, for U.S. Appl. No. 11/436,585, 5 pages.

Gelbart et al., "Method and Device for Closing Holes in Tissue," Amendment filed Jun. 2, 2009, for U.S. Appl. No. 11/436,585, 7 pages.

(56) References Cited

OTHER PUBLICATIONS

Gelbart et al., "Method and Device for Closing Holes in Tissue," Office Action mailed Jul. 7, 2009, for U.S. Appl. No. 11/436,585, 9 pages.
Gelbart et al., "Method and Device for Closing Holes in Tissue," Amendment filed Oct. 26, 2009, for U.S. Appl. No. 11/436,585, 13 pages.
International Search Report, mailed Jan. 8, 2007, for PCT/CA2006/001123, 5 pages.
International Search Report, mailed Sep. 4, 2009, for PCT/US2009/043612, 7 pages.
Jatene, "Left Ventricular Aneurysmectomy," *Journal of Thoracic and Cardiovascular Surgery* 89(3):321-331, 1985.
Konings et al., "Development of an Intravascular Impedance Catheter for Detection of Fatty Lesions in Arteries," *IEEE Transactions on Medical Imaging*, 16(4):439-446, 1997.
Lichtenstein, "Method and Apparatus for Percutaneous Reduction of Anterior-Posterior Diameter of Mitral Valve," U.S. Appl. No. 10/690,131, filed Oct. 20, 2003, 31 pages.
Lichtenstein, "Method and Apparatus for Percutaneous Reduction of Anterior-Posterior Diameter of Mitral Valve," Office Action mailed May 15, 2006, for U.S. Appl. No. 10/690,131, 9 pages.
Lichtenstein, "Method and Apparatus for Percutaneous Reduction of Anterior-Posterior Diameter of Mitral Valve," U.S. Appl. No. 11/400,260, filed Apr. 10, 2006, 32 pages.
Lichtenstein, "Method and Apparatus for Percutaneous Reduction of Anterior-Posterior Diameter of Mitral Valve," Office Action mailed Dec. 1, 2008, for U.S. Appl. No. 11/400,260, 10 pages.
Lichtenstein et al., "Method for Anchoring a Mitral Valve," U.S. Appl. No. 11/475,978, filed Jun. 28, 2006, 15 pages.
Lichtenstein et al., "Method for Anchoring a Mitral Valve," Office Action mailed May 1, 2009, for U.S. Appl. No. 11/475,978, 6 pages.
Lichtenstein et al, "Method for Anchoring a Mitral Valve," Amendment filed Aug. 31, 2009, for U.S. Appl. No. 11/475,978, 24 pages.
Lichtenstein et al, "Method for Anchoring a Mitral Valve," Office Action mailed Dec. 29, 2009, for U.S. Appl. No. 11/475,978, 7 pages.
Lichtenstein et al., "System for Improving Diastolic Dysfunction," U.S. Appl. No. 11/497,309, filed Aug. 2, 2006, 13 pages.
Mack, "New Techniques for Percutaneous Repair of the Mitral Valve," *Heart Failure Review*, 11:259-268, 2006.
Menicanti et al., "The Dor Procedure: What has Changed After Fifteen Years of Clinical Practice?" *Journal of Thoracic and Cardiovascular Surgery* 124(5):886-890, Nov. 2002.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Rivera et al., "Ventricular Aneurysms and Akinesis," *Cleveland Clinic Quarterly* 45(1):133-135, 1978.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.
Timek et al., "Septal-Lateral Annular Cinching Abolishes Acute Ischemic Mitral Regurgitation," *Journal of Thoracic and Cardiovascular Surgery*, 123(5):881-888, 2002.
Torrent-Guasp et al., "Spatial Orientation of the Ventricular Muscle Band and Approach to Partial Ventriculotomy in Heart Failure," *Pathogenesis and Treatment*, Ch. 36, pp. 685-693.

Valvano et al., "Thermal Conductivity and Diffusivity of Biomaterials Measured with Self-Heated Thermistors," *International Journal of Thermodynamics*, 6(3):301-311, 1985.
Written Opinion, mailed Jan. 8, 2007, for PCT/CA2006/001123, 6 pages.
Written Opinion, mailed Sep. 4, 2009, for PCT/US2009/043612, 6 pages.
Gelbart et al, "Method and Device for Closing Holes in Tissue," Office Action mailed Feb. 23, 2012, for U.S. Appl. No. 12/777,883, 8 pages.
Gelbart et al, "Method and Device for Closing Holes in Tissue," Amendment filed May 4, 2012, for U.S. Appl. No. 12/777,883, 12 pages.
"Constellation Mapping Catheters", Brochure, Boston Scientific Corp., 2 pgs, © 2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
Dahlgren et al., "Medical Device for Constricting Tissue or a Bodily Orifice, for Example a Mitral Valve", Amendment filed Aug. 8, 2013 for U.S. Appl. No. 12/899,407, 65 pages.
Dahlgren et al., "Medical Device for Constricting Tissue or a Bodily Orifice, for Example a Mitral Valve", Amendment filed Dec. 13, 2012 for U.S. Appl. No. 12/899,407, 22 pages.
Dahlgren et al., "Medical Device for Constricting Tissue or a Bodily Orifice, for Example a Mitral Valve", Office Action mailed Mar. 8, 2013 for U.S. Appl. No. 12/899,407, 23 pages.
Dahlgren et al., "Medical Device, Kit and Method for Constricting Tissue or a Bodily Orifice, For Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, For Example a Mitral Valve", Final Office Action mailed Feb. 13, 2013 for U.S. Appl. No. 12/894,912, 35 pgs.
Dahlgren et al., "Medical Device, Kit and Method for Constricting Tissue or a Bodily Orifice, For Example a Mitral Valve", Office Action mailed Aug. 30, 2012 for U.S. Appl. No. 12/894,912, 16 pgs.
Dahlgren et al., "Medical Device, Kit and Method for Constricting Tissue or a Bodily Orifice, For Example a Mitral Valve", Response filed Jun. 13, 2013 for U.S. Appl. No. 12/894,912, 3 pgs.
Dahlgren et al., "Medical Device, Kit and Method for Constricting Tissue or a Bodily Orifice, for Example, a Mitral Valve", Office Action mailed Jul. 9, 2014 for U.S. Appl. No. 13/917,469, 37 pgs.
Dahlgren et al., "System for Mechanical Adjustment of Medical Implants", Amendment filed Apr. 2, 2010 for U.S. Appl. No. 11/902,099, 19 pgs.
Dahlgren et al., "System for Mechanical Adjustment of Medical Implants", Amendment filed Nov. 1, 2010 for U.S. Appl. No. 11/902,099, 12 pgs.
Dahlgren et al., "System for Mechanical Adjustment of Medical Implants", Office Action mailed Jul. 8, 2010 for U.S. Appl. No. 11/902,099, 37 pgs.
Dahlgren et al., "System for Mechanical Adjustment of Medical Implants", Office Action mailed Oct. 5, 2009 for U.S. Appl. No. 11/902,099, 13 pgs.
European Search Report, mailed Jun. 26, 2008 for EP 08100878.1, 11 pgs.
Gelbart, "System for Implanting a Microstimulator", Amendment filed Jan. 20, 2010 for U.S. Appl. No. 12/068,878, 26 pgs.
Gelbart, "System for Implanting a Microstimulator", Office Action mailed Aug. 18, 2010 for U.S. Appl. No. 12/068,878, 11 pgs.
Gelbart, "System for Implanting a Microstimulator", Office Action mailed Aug. 20, 2009 for U.S. Appl. No. 12/068,878, 12 pgs.
Goertzen et al., "Tissue Anchor System", Amendment filed Apr. 29, 2013 for U.S. Appl. No. 13/247,380, 22 pgs.

(56) References Cited

OTHER PUBLICATIONS

International Search Report mailed Dec. 6, 2004 for PCT/IB2004/002581, 3 pgs.
Lichtenstein "Closing Openings in Anatomical Tissue", Amendment filed Aug. 8, 2013 for U.S. Appl. No. 13/112,695, 23 pgs.
Lichtenstein "Closing Openings in Anatomical Tissue", Office Action mailed May 8, 2013 for U.S. Appl. No. 13/112,695, 12 pgs.
Lichtenstein et al., "System for Improving Diastolic Dysfunction", Office Action mailed Jan. 29, 2014 for U.S. Appl. No. 12/904,885, 38 pgs.
Lichtenstein et al., "System for Improving Diastolic Dysfunction", Office Action mailed Sep. 18, 2012 for U.S. Appl. No. 12/904,885, 15 pgs.
Lichtenstein et al., "System for Improving Diastolic Dysfunction", Preliminary Amendment filed Oct. 14, 2010 for U.S. Appl. No. 12/904,885, 23 pgs.
Lichtenstein, "Closing Openings in Anatomical Tissue", Final Office Action mailed Dec. 4, 2013 for U.S. Appl. No. 13/112,695, 31 pages.
Lichtenstein, "Methods and Devices for Altering Blood Flow Through the Left Ventricle", Amendment filed Jul. 26, 2007 for U.S. Appl. No. 10/622,129, 17 pages.
Lichtenstein, "Methods and Devices for Altering Blood Flow Through the Left Ventricle", Examiner's Amendment mailed Mar. 2, 2009, for U.S. Appl. No. 10/622,129, 5 pages.
Lichtenstein, "Methods and Devices for Altering Blood Flow Through the Left Ventricle", Office Action mailed Jul. 9, 2010 for U.S. Appl. No. 10/571,165, 11 pages.
Lichtenstein, "Methods and Devices for Altering Blood Flow Through the Left Ventricle", Office Action mailed Mar. 26, 2007 for U.S. Appl. No. 10/622,129, 17 pages.
Lichtenstein, "Methods and Devices for Altering Blood Flow Through the Left Ventricle", Office Action mailed Nov. 14, 2007 for U.S. Appl. No. 10/622,129, 6 pages.
Lichtenstein, "Methods and Devices for Altering Blood Flow Through the Left Ventricle", Preliminary Amendment filed Feb. 14, 2008 for U.S. Appl. No. 10/622,129, 15 pages.
Lichtenstein, "Methods and Devices for Altering Blood Flow Through the Left Ventricle", Preliminary Amendment filed Mar. 6, 2006 for U.S. Appl. No. 10/571,165, 7 pages.
STAR CLOSE Vascular Closure System Brochure, 2005, Abbott Vascular, pp. 1-4.
Tegzes, "Medical Kit for Constricting Tissue or a Bodily Orifice, for Example, a Mitral Valve", Office Action mailed Jul. 11, 2014 for U.S. Appl. No. 13/421,677, 9 pgs.
Written Opinion mailed Dec. 6, 2004 for PCT/IB2004/002581, 8 pgs.
Becker, et al., "Ablation of Atrial Fibrillation: Energy Sources and Navigation Tools: A Review", Journal of Electrocardiology, vol. 37, Supplement 2004, pp. 55-62, 2004.
Calkins, Hugh, "Electrophysiology: Radiofrequency Catheter Ablation of Supraventricular Arrhythmias", Heart, 2001; 85; pp. 594-600.
Dahlgren et al, "Medical Device for Constricting Tissue or a Bodily Orifice, for Example a Mitral Valve", Office Action mailed Sep. 13, 2012 for U.S. Appl. No. 12/899,407, 28 pgs.
Dahlgren et al., "Medical Device for Constricting Tissue or a Bodily Orifice, for Example a Mitral Valve", Amendment filed Jul. 23, 2013 for U.S. Appl. No. 12/899,407, 60 pages.
Dahlgren et al., "Medical Device, Kit and Method for Constricting Tissue or a Bodily Orifice, for Example, a Mitral Valve", Amendment filed Dec. 30, 2014 for U.S. Appl. No. 13/917,469, 18 pages.
De Ponti, et al., "Non-Fluoroscopic Mapping Systems for Electrophysiology: the Tool or Toy Dilemma After 10 Years", European Heart Journal, 2006; 27, pp. 1134-1136.
Extended European Search Report mailed Sep. 18, 2014 for EP 10821276.2, 10 pages.
Gabriel, et al., "The Dielectric Properties of Biological Tissues: I. Literature Survey", Phys. Med. Biol.; 41, 1996, pp. 2231-2249.

Gelbart et al., "Automatic Atherectomy System", Amendment filed Oct. 25, 2010 for U.S. Appl. No. 11/436,584, 9 pgs.
Gelbart et al., "Automatic Atherectomy System", Amendment filed Mar. 30, 2010 for U.S. Appl. No. 11/436,584, 20 pgs.
Gelbart et al., "Automatic Atherectomy System", Amendment filed Aug. 4, 2009 for U.S. Appl. No. 11/436,584, 35 pgs.
Gelbart et al., "Automatic Atherectomy System", Amendment filed Sep. 15, 2011 for U.S. Appl. No. 12/950,871, 21 pgs.
Lichtenstein et al., "System for Improving Diastolic Dysfunction", Office Action mailed Apr. 10, 2015 for U.S. Appl. No. 12/904,885, 67 pages.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Lopes et al., "Enhanced Medical Device for Use in Bodily Cavities, for Example an Atrium", U.S. Appl. No. 61/435,213, filed Jan. 21, 2011, 320 pgs.
Lopes et al., "Enhanced Medical Device for Use in Bodily Cavities, for Example an Atrium", U.S. Appl. No. 61/485,987, filed May 13, 2011, 401 pgs.
Lopes et al., "Enhanced Medical Device for Use in Bodily Cavities, for Example an Atrium", U.S. Appl. No. 61/488,639, filed May 20, 2011, 434 pgs.
Lopes et al., "Enhanced Medical Device for Use in Bodily Cavities, for Example an Atrium", U.S. Appl. No. 61/515,141, filed Aug. 4, 2011, 508 pgs.
Mazur et al., "Bone Fixation Device, Tools and Methods", U.S. Appl. No. 61/138,920, filed Dec. 18, 2008, 88 pgs.
Tegzes, "Medical Kit for Constricting Tissue or a Bodily Orifice, for Example, a Mitral Valve", Amendment filed Dec. 3, 2014 for U.S. Appl. No. 13/421,677, 17 pgs.
Tegzes, "Medical Kit for Constricting Tissue or a Bodily Orifice, for Example, a Mitral Valve", U.S. Appl. No. 61/467,883, filed Mar. 25, 2011, 167 pgs.
Written Opinion mailed Jun. 16, 2011 for PCT/US2010/050945, 4 pgs.
Written Opinion mailed Sep. 10, 2010 for PCT/US2010/021835, 6 pgs.
Written Opinion, mailed Dec. 2, 2009, for PCT/US2008/083644, 9 pages.
Written Opinion, mailed Dec. 5, 2007, for PCT/US2007/014902, 7 pages.
Dahlgren et al., "Medical Device, Kit and Method for Constricting Tissue or a Bodily Orifice, for Example, a Mitral Valve", Office Action mailed Mar. 5, 2015 for U.S. Appl. No. 13/917,469, 52 pgs.
Lichtenstein et al., "Method for Anchoring a Mitral Valve", Office Action mailed Apr. 24, 2015 for co-pending U.S. Appl. No. 14/162,469, 61 pages.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance mailed Aug. 20, 2010 for U.S. Appl. No. 11/436,584, 12 pgs.
Gelbart et al., "Automatic Atherectomy System", Notice of Allowance mailed May 10, 2013 and Certificate of Correction mailed May 6, 2014 for U.S. Appl. No. 13/404,834, 11 pgs.
Gelbart et al., "Automatic Atherectomy System", Notice of Allowance mailed Nov. 25, 2011 and Certificate of Correction mailed Jul. 17, 2012 for U.S. Appl. No. 12/950,871, 24 pgs.
Gelbart et al., "Automatic Atherectomy System", Office Action mailed Dec. 1, 2009 for U.S. Appl. No. 11/436,584, 8 pgs.
Gelbart et al., "Automatic Atherectomy System", Office Action mailed Dec. 14, 2010 for U.S. Appl. No. 11/436,584, 12 pgs.
Gelbart et al., "Automatic Atherectomy System", Office Action mailed Mar. 4, 2009 for U.S. Appl. No. 11/436,584, 6 pgs.
Gelbart et al., "Automatic Atherectomy System", Office Action mailed Jun. 15, 2011 for U.S. Appl. No. 12/950,871, 16 pgs.
Gelbart et al., "Automatic Atherectomy System", Office Action mailed Sep. 25, 2012 for U.S. Appl. No. 13/404,834, 24 pgs.
Gelbart et al., "Intra-Cardiac Mapping and Ablation Method", Amendment filed Feb. 23, 2011 for U.S. Appl. No. 11/475,950, 28 pgs.

(56) References Cited

OTHER PUBLICATIONS

Gelbart et al., "Intra-Cardiac Mapping and Ablation Method", Amendment filed Mar. 5, 2008 for U.S. Appl. No. 11/475,950, 11 pgs.
Gelbart et al., "Intra-Cardiac Mapping and Ablation Method", Amendment filed Aug. 16, 2010 for U.S. Appl. No. 11/475,950, 22 pgs.
Gelbart et al., "Intra-Cardiac Mapping and Ablation Method", Office Action mailed Nov. 23, 2010 for U.S. Appl. No. 11/475,950, 25 pgs.
Gelbart et al., "Intra-Cardiac Mapping and Ablation Method", Office Action mailed Jun. 23, 2010 for U.S. Appl. No. 11/475,950, 18 pgs.
Gelbart et al., "Intra-Cardiac Mapping and Ablation Method", Pre Amend filed Aug. 29, 2007 for U.S. Appl. No. 11/475,950, 42 pgs.
Gelbart et al., "Liposuction System", Amendment filed Dec. 7, 2011 for U.S. Appl. No. 12/010,458, 15 pgs.
Gelbart et al., "Liposuction System", Amendment filed Jun. 10, 2011 for U.S. Appl. No. 12/010,458, 10 pgs.
Gelbart et al., "Liposuction System", Office Action mailed Mar. 16, 2011 for U.S. Appl. No. 12/010,458, 12 pgs.
Gelbart et al., "Liposuction System", Office Action mailed Sep. 14, 2011 for U.S. Appl. No. 12/010,458, 9 pgs.
Gelbart et al., "Medical Device for Use in Bodily Lumens, for Example an Atrium", Office Action mailed Jul. 25, 2011 for U.S. Appl. No. 11/941,819, 9 pgs.
Gelbart et al., "Method and Device for Closing Holes in Tissue", Notice of Allowance mailed Aug. 22, 2012 for U.S. Appl. No. 12/777,883, 12 pgs.
Gelbart et al., "Method and Device for Closing Holes in Tissue", Notice of Allowance mailed Feb. 24, 2010, Supplemental Notice of Allowance mailed Mar. 24, 2010 and Remarks filed after allowance on Apr. 9, 2010 for U.S. Appl. No. 11/436,585, 20 pgs.
Goertzen et al., "Tissue Anchor System", Amendment filed Dec. 10, 2013 for U.S. Appl. No. 13/247,380, 11 pgs.
Goertzen et al., "Tissue Anchor System", Amendment filed Oct. 11, 2013 for U.S. Appl. No. 13/247,380, 10 pgs.
Goertzen et al., "Tissue Anchor System", Notice of Allowance mailed Dec. 3, 2014 for U.S. Appl. No. 13/247,380, 14 pgs.
Goertzen et al., "Tissue Anchor System", Notice of Allowance mailed Jul. 7, 2014 for U.S. Appl. No. 13/247,380, 8 pgs.
Goertzen et al., "Tissue Anchor System", Notice of Allowance mailed Oct. 16, 2014 for U.S. Appl. No. 13/247,380, 41 pgs.
Goertzen et al., "Tissue Anchor System", Office Action mailed Aug. 13, 2013 for U.S. Appl. No. 13/247,380, 15 pgs.
Goertzen et al., "Tissue Anchor System", Office Action mailed Jan. 29, 2013 for U.S. Appl. No. 13/247,380, 10 pgs.
International Preliminary Report on Patentability, issued Jan. 6, 2009 for PCT/US2007/014902, 8 pages.
International Search Report mailed Jun. 16, 2011 for PCT/US2010/050945, 5 pgs.
International Search Report mailed Sep. 10, 2010 for PCT/US2010/021835, 4 pgs.
International Search Report, mailed Dec. 2, 2009 for PCT/US2008/083644, 4 pages.
International Search Report, mailed Dec. 5, 2007 for PCT/US20071014902, 4 pages.
Jaramillo et al, "Surgical Instrument and Method for Tensioning and Securing a Flexible Suture", Amendment filed Dec. 4, 2012 for U.S. Appl. No. 12/436,926, 19 pgs.
Jaramillo et al, "Surgical Instrument and Method for Tensioning and Securing a Flexible Suture", Amendment filed Feb. 27, 2012 for U.S. Appl. No. 12/436,926, 25 pgs.
Jaramillo et al, "Surgical Instrument and Method for Tensioning and Securing a Flexible Suture", Amendment filed Jul. 26, 2011 for U.S. Appl. No. 12/246,614, 41 pgs.
Jaramillo et al, "Surgical Instrument and Method for Tensioning and Securing a Flexible Suture", Amendment filed Mar. 14, 2011 for U.S. Appl. No. 12/246,614, 22 pgs.
Jaramillo et al, "Surgical Instrument and Method for Tensioning and Securing a Flexible Suture", Amendment filed Oct. 5, 2011 for U.S. Appl. No. 12/436,926, 77 pgs.
Jaramillo et al, "Surgical Instrument and Method for Tensioning and Securing a Flexible Suture", Office Action mailed Dec. 13, 2010 for U.S. Appl. No. 12/246,614, 15 pgs.
Jaramillo et al, "Surgical Instrument and Method for Tensioning and Securing a Flexible Suture", Office Action mailed Jan. 11, 2012 for U.S. Appl. No. 12/436,926, 26 pgs.
Jaramillo et al, "Surgical Instrument and Method for Tensioning and Securing a Flexible Suture", Office Action mailed Jul. 8, 2011 for U.S. Appl. No. 12/436,926, 17 pgs.
Jaramillo et al, "Surgical Instrument and Method for Tensioning and Securing a Flexible Suture", Office Action mailed May 27, 2011 for U.S. Appl. No. 12/246,614, 24 pgs.
Jaramillo et al, "Surgical Instrument and Method for Tensioning and Securing a Flexible Suture", Office Action mailed Sep. 21, 2012 for U.S. Appl. No. 12/436,926, 14 pgs.
Lichtenstein et al., "Method for Anchoring a Mitral Valve", Notice of Allowance mailed Jan. 28, 2013 for U.S. Appl. No. 11/475,978, 24 pgs.
Lichtenstein et al., "Method for Anchoring a Mitral Valve", Notices of Allowance mailed Oct. 2, 2013 and Nov. 13, 2013 for U.S. Appl. No. 13/872,870, 35 pgs.
Lichtenstein et al., "Method for Anchoring a Mitral Valve", Preliminary Amendment filed Jan. 24, 2014 for U.S. Appl. No. 14/162,469, 9 pgs.
Lichtenstein et al., "System for Improving Diastolic Dysfunction", Amendment filed Apr. 9, 2014 for U.S. Appl. No. 12/904,885, 24 pgs.
Lichtenstein et al., "System for Improving Diastolic Dysfunction", Amendment filed Dec. 18, 2012 for U.S. Appl. No. 12/904,885, 23 pgs.
Lichtenstein et al., "System for Improving Diastolic Dysfunction", Notice of Allowance mailed Jul. 12, 2010 for U.S. Appl. No. 11/497,309, 8 pgs.
Amendment filed in U.S. Appl. No. 12/899,407 on Jun. 14, 2016.
Office Action issued in U.S. Appl. No. 12/899,407 mailed Sep. 1, 2016.
Dahlgren et al., "Medical Device for Constricting Tissue or a Bodily Orifice, For Example a Mitral Valve", Office Action mailed Dec. 23, 2015 for U.S. Appl. No. 12/899,407, 60 pages.
Dahlgren et al., "Medical Device, Kit and Method for Constricting Tissue or a Bodily Orifice, For Example, A Mitral Valve", Amendment dated Jun. 4, 2015 for U.S. Appl. No. 13/917,469, 17 pages.
Lichtenstein et al., "System for Improving Diastolic Dysfunction", Final Office Action mailed Nov. 23, 2015 for U.S. Appl. No. 12/904,885, 43 pages.
Lichtenstein et al., "Method for Anchoring a Mitral Valve", Amendment dated Jun. 30, 2015 for U.S. Appl. No. 14/162,469, 7 pages.
Lichtenstein, "System for Improving Diastolic Dysfunction", Amendment dated Aug. 10, 2015 for U.S. Appl. No. 12/904,885, 18 pages.

* cited by examiner

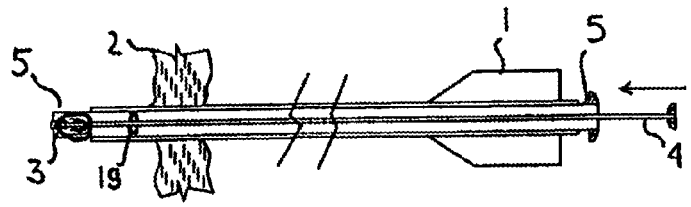
FIG. 2-a
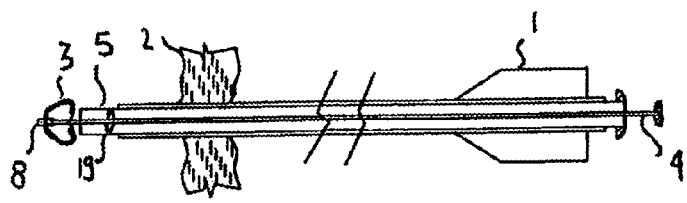
FIG. 2-b
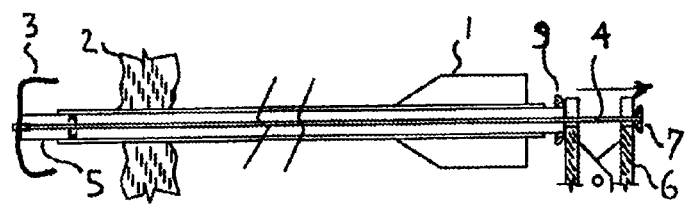
FIG. 2-c
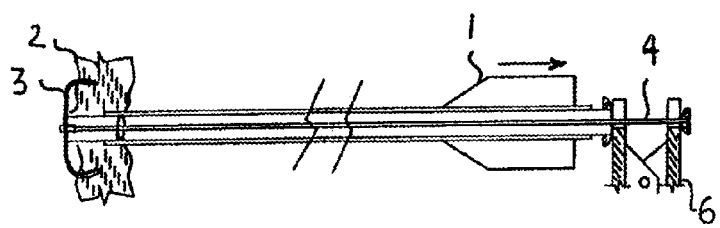
FIG. 2-d
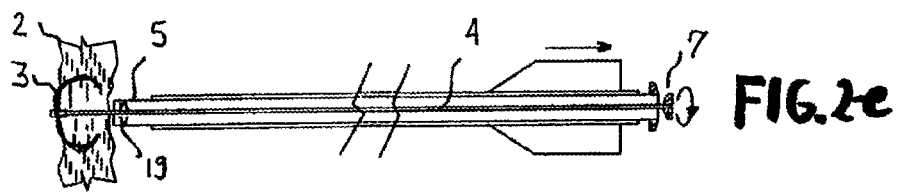
FIG. 2-e
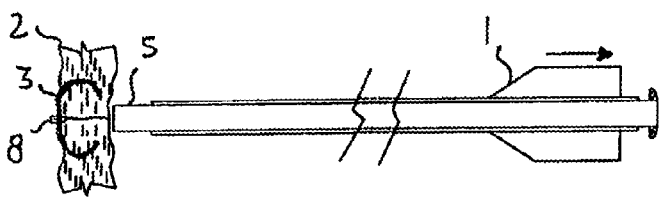
FIG. 2-f

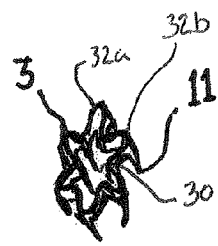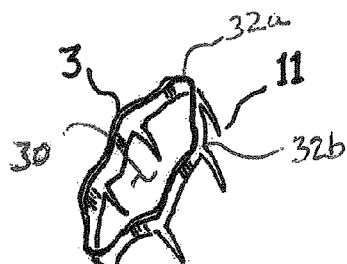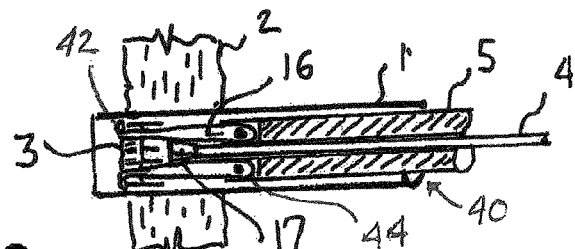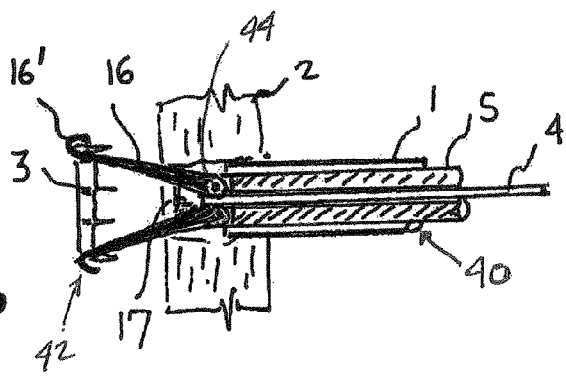

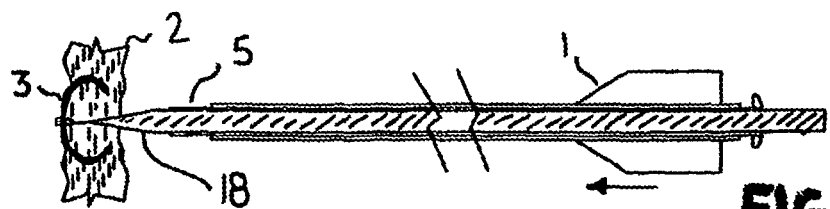
FIG.8-a
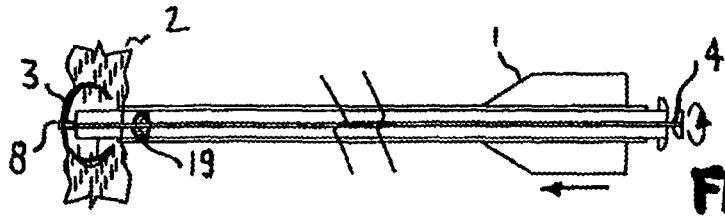
FIG.8-b
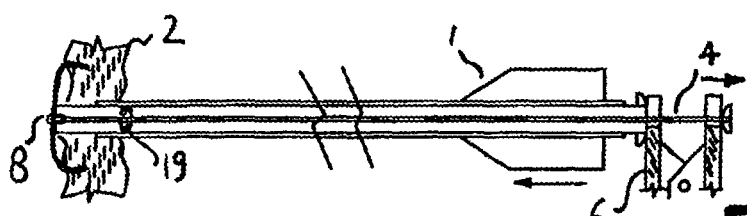
FIG.8-c
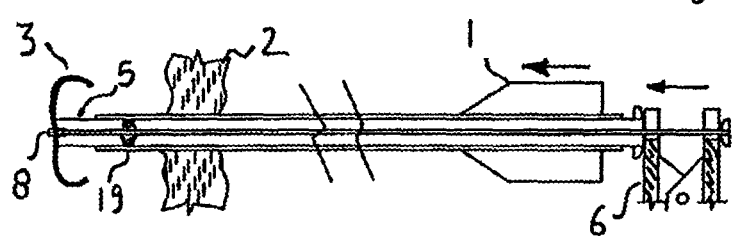
FIG.8-d
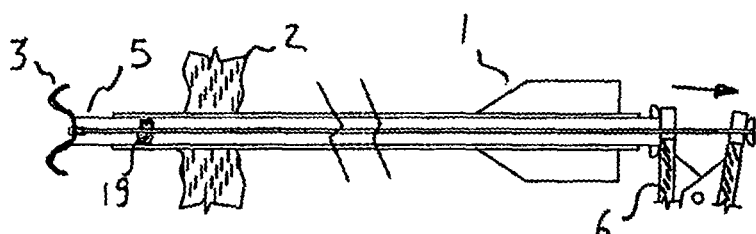
FIG.8-e
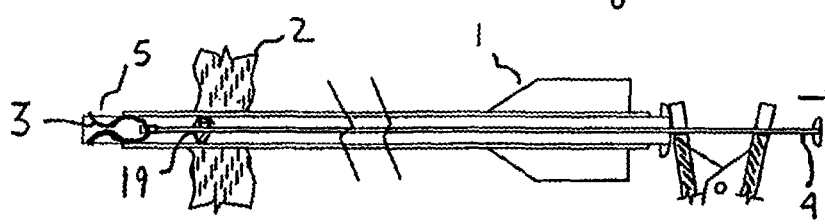
FIG.8-f

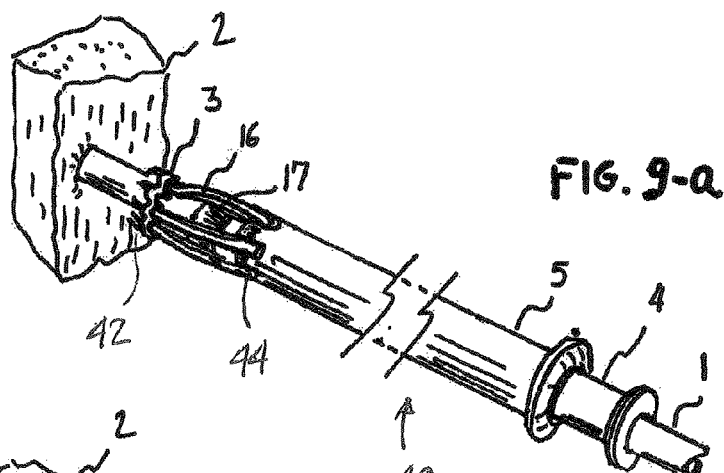
FIG. 9-a
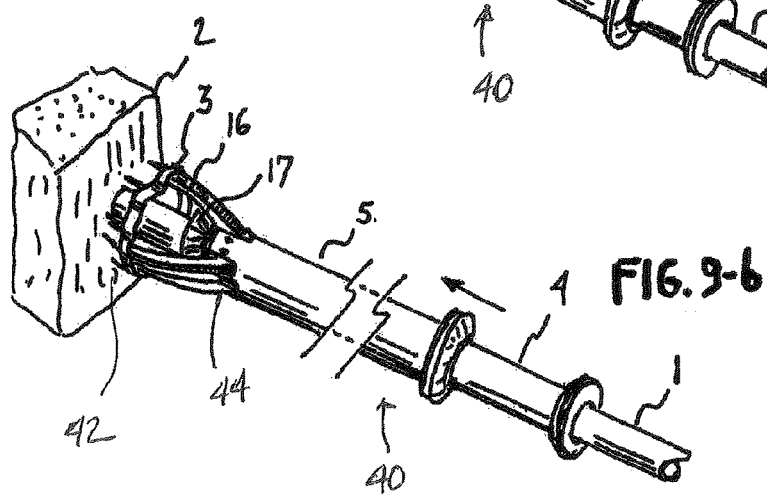
FIG. 9-b

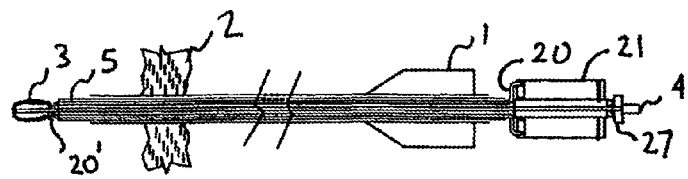
FIG.13-a
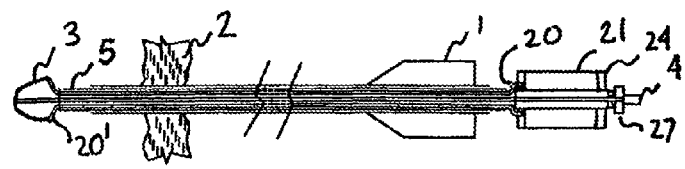
FIG.13-b
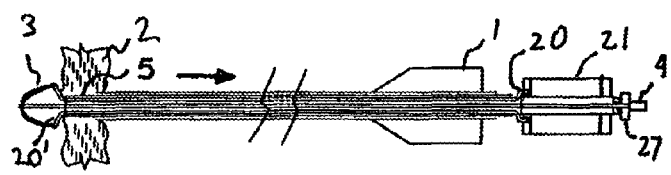
FIG.13-c
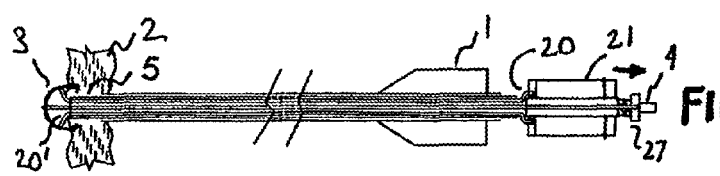
FIG.13-d
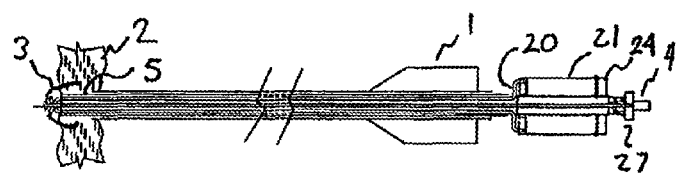
FIG.13-e
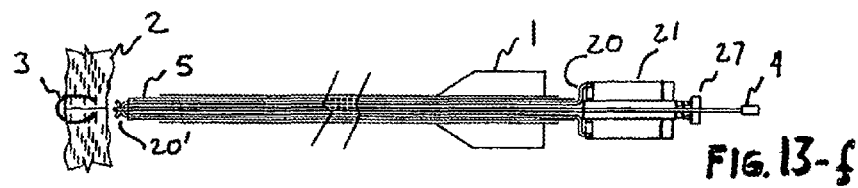
FIG.13-f

METHOD AND DEVICE FOR CLOSING HOLES IN TISSUE

FIELD OF THE INVENTION

The present invention relates to surgery and in particular to closing holes in tissue during minimally invasive surgery. The invention is particularly useful for closing holes left by catheters during percutaneous surgical procedures such as minimally invasive cardiac surgery and other surgeries requiring access to body lumens.

BACKGROUND OF THE INVENTION

More and more surgical procedures are performed percutaneously by the use of catheter-delivered devices. The main advantages are fast patient recovery and lower costs to the medical system. Some tissues, such as muscular tissue or arterial walls, do not seal well and are sometimes subject to blood pressure; therefore they require an immediate hemostatic seal after the surgery. Prior art solutions mainly rely on some form of a plug, such as an expanding foam plug, expanding metal plug or a barbed plug to seal the hole. The main disadvantage of plugs is that in order to form a good seal they are forcing the hole to become larger, rather than the more natural way which is to shrink the hole in order to promote healing. A prior art device operating by shrinking the hole is the Star Closure device sold by Abbott Vascular (www.abbottvasculardevices.com) however this device is only suitable to thin walled body lumens as it relies on folding the tissue. When sealing larger holes in thicker tissue the gripping points for pulling the tissue inwards have to be spread over an area significantly larger than the hole size, similar to what is done in traditional suturing. Attaching the closure device too close to the hole does not allow sufficient forces to be applied, therefore creating a marginal closure.

Another major shortcoming of the Star Closure and other devices is that the operation is not reversible. It is sometimes required to remove the closure, as in the case of bleeding or an additional procedure.

It is therefore desired to provide a hole closure method that provides an immediate liquid and gas tight closure and it can be delivered by a catheter to the inside wall of a body lumen.

It is also desired to provide a closure method suitable for a large range of tissue thicknesses and hole sizes.

It is also desired to be able to test, and if required to remove, the closure.

It further would be desired for the closing device to have permanent elastic properties to accommodate any movement or future changes in the tissue. Furthermore, the gripping area of the closure device has to be significantly larger than the original hole.

SUMMARY OF THE INVENTION

In view of the foregoing, the invention provides a method and device for closing holes in body lumens, and in particular in the heart and blood vessels, achieving an immediate hemostatic seal. The device can be applied via a wide range of catheters sizes to close a wide range of round and elongated holes with performance and reliability of traditional sutures but without requiring access to the tissue, except via the catheter. Furthermore, the device can be removed via the same catheter, and by using the same tools used to install it and can be re-used immediately if so desired. The device has a high degree of elastic compliance allowing a wide accommodation range to changes in the tissue. These and other objects of the present invention are achieved by providing a flexible clip that is temporarily attaches to an insertion tool. The clip has three different positions: a storage position, in which it is folded inside a delivery tube; an expanded position, in which it opens up to reach an area significantly larger than the hole, and a closed position in which elastic forces try to close the clip, pulling the tissue with it to close the hole. The clip has multiple sharp barbs for gripping the tissue and a stem for attaching to the insertion tool, as well as for re-attaching in case removal is required.

Methods for implanting and removal of the device are also provided.

The invention will become apparent by studying the drawings and the detailed description.

BRIEF DESCRIPTION OF THE DRAWING

FIG. 2-a to FIG. 2-f are sectional views showing the steps in installing the device using the installation tool.

FIG. 6-a is a perspective view of an alternate embodiment in the relaxed state.

FIG. 6-b is a perspective view of the same alternate embodiment in the expanded state.

FIG. 7-a is a sectional view of the tool used to install the device embodiment of FIG. 6-a in the relaxed state.

FIG. 7-b is a sectional view of the tool used to install the device embodiment of FIG. 6-a in the expanded state.

FIG. 8-a to FIG. 8-f are sectional views showing the steps in removing the device, FIG. 9-a and FIG. 9-b are perspective views of a device installed on the outside of a catheter.

FIG. 12-b is a perspective view of the preferred embodiment in the retracted position.

FIG. 13-a to FIG. 13-f are sectional view of the preferred embodiment showing the steps in installing the device.

DETAILED DESCRIPTION OF THE INVENTION

Figure 1:
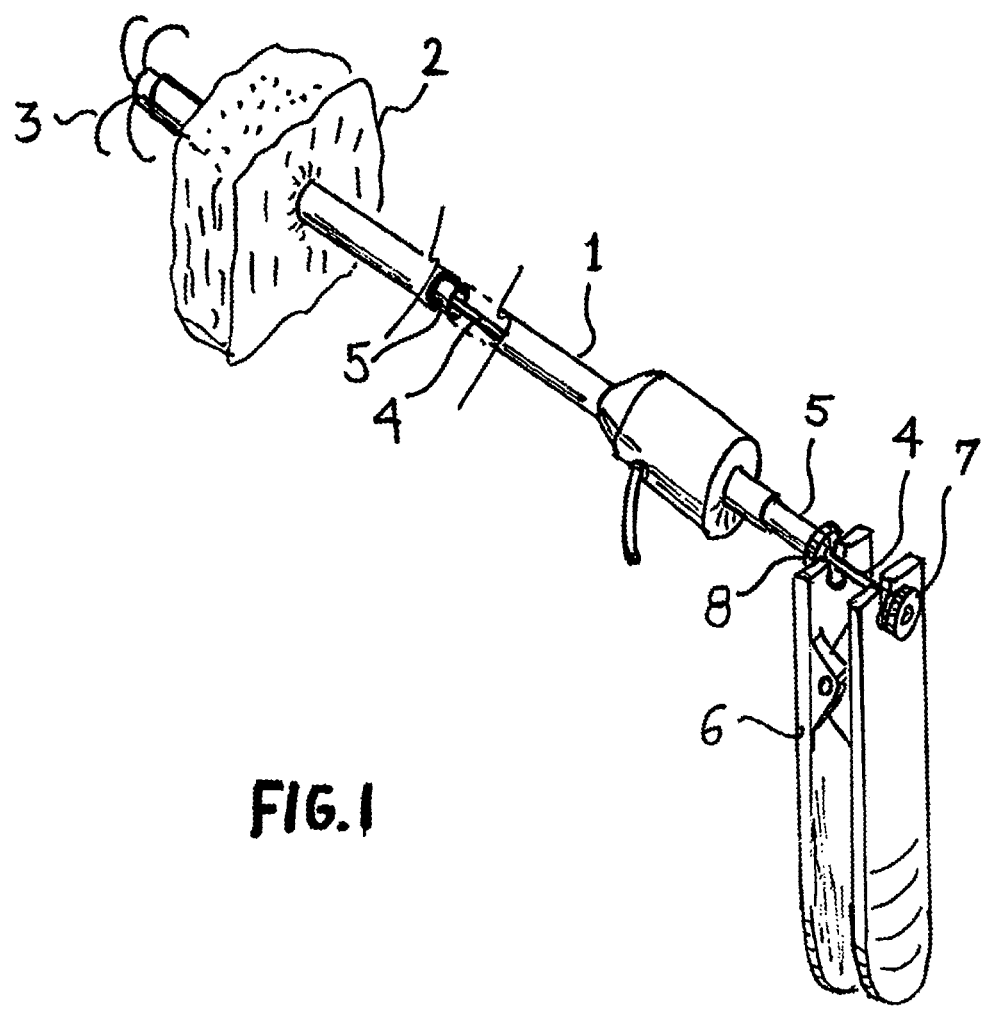
FIG. 1 is a perspective view of the invention and the installation tool.

Referring to FIG. 1, a hole closure clip 3 is inserted into a body lumen such a cavity in the heart via catheter 1. Catheter 1 has a seal allowing insertion and removal of tools without much blood loss. This is well known in the art of minimally invasive surgery. When the surgical procedure is completed and hole needs to be closed, tube 5 carrying clip 3 mounted on rod 4 is inserted via catheter 1 through the tissue 2. Both rod 4 and tube 5 have flanges 7 and 8 allowing a pulling tool 6 to exert a significant pulling force on rod 4 relative to tube 5. Pulling tool 6 may be made of plastic or metal, plastic being preferred if tool is to be disposable. Rod 4 and tube 5 are preferable made of stainless steel and closure device 3 is made of Nitinol, a highly flexible Nickel-Titanium alloy well known in the art of medical devices. Tool 6 is similar in construction to the well known clothespin. Since the elastic range of Nitinol is about ten times larger than steel, the clip 3 can be made to fold into a small diameter tube and expand to grip the tissue over an area significantly larger than the area of the hole, in order to establish reliable closure. When clip 3 is released it tries to return to its natural (relaxed) shape, which covers a significantly smaller area, pulling the tissue with it and forming an instant hemostatic seal. These steps are shown in FIG. 2-*a* to FIG. 2-*f*.

Figure 3:
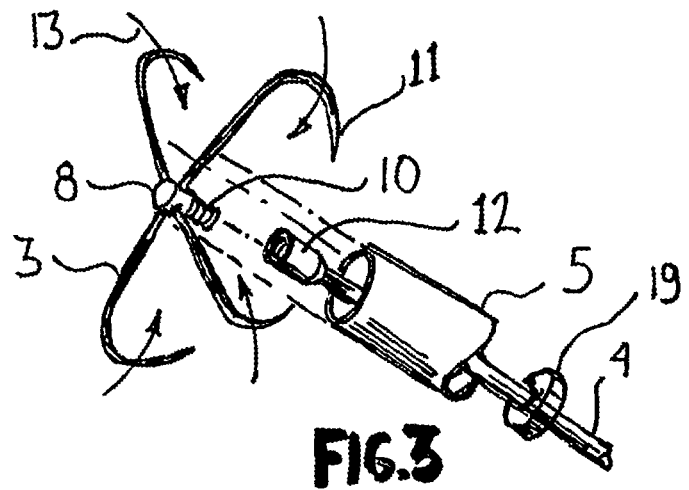
FIG. 3 is a perspective "exploded" view of the device.

In FIG. 2-*a* the tube 5 containing the folded clip 3 mounted on rod 4 is inserted via catheter 1 through the wall of the tissue 2. Rod 4 is pushed forward by finger pressure till it is felt that clip 3 is released from tube 5 (or moved till it reaches a pre-determined distance), as shown in FIG. 2-*b*. At this point it is pulled back and pulling tool 6 is installed by sliding it on rod 4. Pulling tool 6 can be permanently mounted on rod 4 or slide in and out via two slots as shown in FIG. 1. The slots rest against flanges 7 and 8. Flange 7 is rigidly connected to rod 4 while flange 8 is rigidly connected to tube 5. Using pulling tool 6, rod 4 is pulled out a pre-determined amount which forces clip 3 to open as shown in FIG. 2-*c*, as it rests against end of tube 5. At this point the whole assembly, including catheter 1, is pulled back to engage the sharp barbs of tool 3 in tissue 2. This is shown in FIG. 2-*d*. An enlarged view of clip 3 is shown in FIG. 3. In FIG. 3, clip 3 comprises of multiple sharp barbs 11 held by a threaded stem 8. Clip 3, including barbs 11 are made of Nitinol wire typically 0.3-0.8 mm in diameter, Stem 8 can be made of type 316 stainless steel and held to wires by crimping. It contains a threaded portion 10 for attaching to rod 4. The end of rod 4 has a mating thread 12. When clip 3 rests on edge of tube 5 it can be opened widely by pulling rod 4 and barbs 11 can reach over an area having a diameter from 1.5 to over 3 times the diameter of the hole. This is important to achieve proper hemostatic closure. When rod 4 is detached from clip 3, the natural elasticity pulls barb 11 in the direction shown by arrows 13 and the tissue is pulled with them. Centering ferrule 19 on rod 4 keeps the location of clip 3 centered to tube 5, therefore centered to hole in tissue. Returning now to FIG. 2-*e*, pulling tool 6 is released and removed allowing clip 3 to compress the tissue. Rod 4 is removed by turning flange 7 to unthread rod. After rod is removed the closure can be tested for leaks by leaving tube 5 in place. When used in the heart, any imperfection in closure will cause blood to come out of tube 5. In such a case the clip 3 can be removed and re-installed as shown later on in this disclosure. One verified, both tube 5 and catheter 1 are removed.

Figure 4:
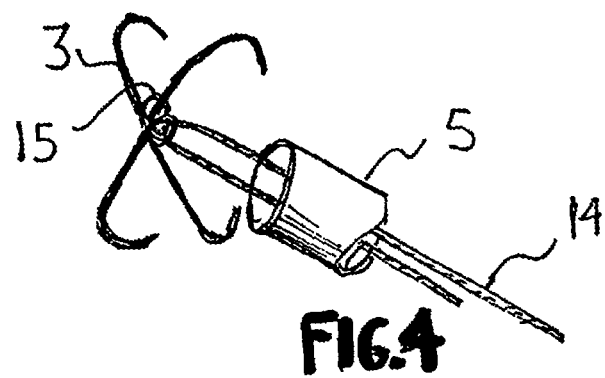
FIG. 4 is a perspective "exploded" view of an alternate embodiment.

FIG. 4 shows an alternate design for clip 3. The main differences are that the Nitinol wire is bent into a loop 15 to add elasticity and a string 14 is used as a method of holding clip 3 to tube 5. The string can be removed by releasing one end.

Figure 5:
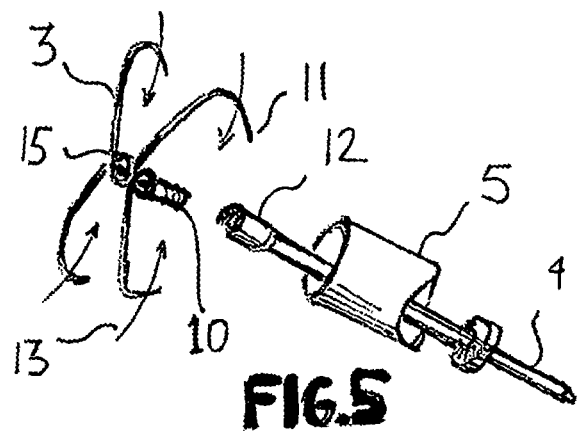
FIG. 5 is an "exploded" view of another alternate embodiment.

FIG. 5 shows another alternate design, preferred when hole is an elongated cut rather than a round hole. Clip 3 is bent to have barbs 11 move in parallel rather than radially, as shown by arrows 13. Clip 3 is placed with the direction of motion 11 perpendicular to long dimension of hole in tissue. Loops 15 are used to add elasticity, as in FIG. 4.

FIGS. 6-*a* and 6-*b* show yet another alternate design. The clip 3 can be fabricated from Nitinol sheet, tubing or wire. The preferred way would be laser-cut tubing. FIG. 6-*a* shows the clip in the relaxed state, FIG. 6-*b* shows it in the expanded state. This design is suitable when a large number of barbs 11 are desired or for thin-walled lumens. In some embodiments (e.g., as shown in FIGS. 6-*a* and 6-*b*), a portion of a closure device in the form of clip 3 forms at least a part of a periphery of a central passage 30, the at least part of the periphery of the central passage located radially inward from the plurality of barbs 11 at least in a second configuration (FIG. 6-*a*). In some embodiments (e.g., as shown in FIGS. 6-*a* and 6-*b*), the closure device (e.g., clip 3) may take the form of a closed band having a plurality of lobes 32*a*, 32*b* (i.e., multi-lobed, only two called out for sake of clarity of illustration, collectively referenced as 32), with a respective barb 11 extending from each lobe 32. In some embodiments (e.g., as shown in FIGS. 6-*a* and 6-*b*), each barb 11 extends generally parallel to a direction through the central passage 30 along which portion the at least one tool (See for example FIGS. 7-*a*, 7-*b*, 9-*a*, 9-*b*) is selectively removable receivable in each of a first configuration (e.g., FIGS. 6-*b*, 7-*b*, 9-*b*) in which a radial size of the central passage has a first dimension and second configuration (e.g., FIGS. 6-*a*, 7-*a*, 9-*a*) in which the radial size of the central passage has a second dimension, the second dimension smaller than the first dimension. In at least some embodiments (e.g., FIGS. 6-*a* and 6-*b*), each barb 11 is radially spaced outwardly from a longitudinal axis of the central passage 30 by a respective first radial distance when in a relaxed state and by a corresponding second radial distance in an expanded state, each first radial distance smaller than a corresponding second radial distance. In at least some embodiments, at least part of the periphery of the central passage 30 is located radially inward from the plurality of barbs 11 by a first distance in the expanded state (e.g., FIG. 6-*b*) and by a second distance in the relaxed state (e.g., FIG. 6-*a*), the first distance being smaller than the second distance.

The tool used to expand the Clip is shown in FIG. 7-*a* (relaxed state) and FIG. 7-*b* (expanded state). Rod 4 is equipped with a tapered end 17 used to expand four pivoting arms 16. The sequence of operations is identical to the sequence shown in FIG. 2-*a* to FIG. 2-*f*. In some embodiments (e.g., FIGS. 7-*a*, 7-*b*, 9-*a*, 9-*b*), at least one tool 40 cooperatively engages at least part of the periphery of the central passage 30 of the closure device (e.g., clip 3), to move the closure device from the second configuration (e.g., FIGS. 7-*a*, 9-*a*) to the first configuration (e.g., FIGS. 7-*b*, 9-*b*) during use. In the illustrated embodiment the tool 40 includes four arms 16, each with respective distal end 42, and proximate end 44. As is visible in FIGS. 7-*a*, 7-*b*, 9-*a*, 9-*b*, the distal ends 42 engage the dosed band of the closure device (e.g., clip 3) during implantation of the closure device, the proximate ends 44 are pivotally coupled such that the distal ends 42 are radially spaceable from one another between a retracted configuration (e.g., FIG. 7-*a*, 9-*a*) and an expanded configuration (e.g., FIG. 7-*b*, 9-*b*) to move the closure device (e.g., clip 3) from the second configuration (FIGS. 6-*a*, 7-*a*, 9-*a*) to the first configuration (FIGS. 6-*b*, 7-*b*, 9-*b*). As visible in FIGS. 7-*a*, 7-*b*, 9-*a*, 9-*b*, the tool 40 may include a taper element 17 mounted for translation along at least one catheter 1, and which physically engages the arms 16 of the at least one tool 40 to cause the arms 16 to pivot between the retracted and the expanded configurations (FIGS. 7-*a*, 9-*a*, 7-*b*, 9-*b*, respectively). As illustrated in FIGS. 7-*a*, 7-*b*, 9-*a*, 9-*b*, the taper element 17 may be at a distal end of a rod 4. As illustrated in FIGS. 9-*a*, 9-*b*, the rod 4 may have a longitudinal passage that slideably receives the at least one catheter 1, the rod 4 slideably received through a passage in a tube 5 to which the arms 16 are pivotally coupled. As illustrated in at least FIGS. 9-*a*, 9-*b*, the at least one tool 40 engages at least part of a peripheral portion forming at least part of a periphery of the central passage 30 (FIGS. 6-*a*, 6-*b*) in an arrangement that avoids any contact with a tissue-penetrating tip of each respective barb of the clip 3 during movement between the second configuration (e.g., at least FIGS. 6-*a*, 9-*a*) and the first configuration (e.g., at least FIGS. 6-*b*, 9-*b*).

It is desirable to be able to reverse the clip installation and, if needed, remove the clip completely via the same catheter used to install it. The current invention, in all its forms, allows this to be done. Referring now to FIG. 8-*a* to FIG. 8-*f*: the sequence of partial and full removal is shown.

In FIG. 8-*a* a dilator 18 is used to expand the opening in the tissue 2 as well as the surrounding tissue, in order to feed tube 5 back into its original position. In FIG. 8-*b* Rod 4 is inserted in tube 5 and is attached to clip 3 by threading it onto stem 8 of clip 3. Centering ferrule 19 keeps rod 4 aligned with stem 8. Tool 6 in mounted on rod 4 and used to expand clip 3 as shown in FIG. 8-*c*. Once expanded, the whole assembly of catheter 1 and tube 5 is pushed forward to remove clip 3 from tissue 2, as shown in FIG. 8-*d*. At this point clip 3 can be re-installed following the steps in FIG. 2-*c* to FIG. 2-*f* or removed completely by pulling clip into tube 5 as shown in FIG. 8-*e* and FIG. 8-*f*. Once clip 3 is fully inside tube 5, it can be easily pulled out by hand using rod 4. If desired, clip 3 can be re-used immediately by pushing it back into tube 5 to assume the position shown in FIG. 2-*a*. When the clip style shown in FIG. 4 is used, the retrieval tool is equipped with a small hook to engage with loop 15.

The large elastic range of Nitinol allows full removal without permanently deforming clip 3. Because of this large elasticity, clip 3 can not be manufactured by cold forming. It has to be held in the relaxed position (shown in FIG. 2-*b*) and heated to about 510 degrees C. for a few minutes. The exact heat treatment details given by the manufacturer of the Nitinol wire have to be carefully followed.

While the invention will work for any dimension of catheter, the preferred range is for catheters with internal diameters of 4 mm to 15 mm. The Nitinol wire diameter is about 0.4 mm for the 4 mm catheter and about 1 mm for the 15 mm catheter. The thread 10 on stem 8 is from M1 for the 4 mm catheter to M4 on the 15 mm catheter, M2 being a typical value. Tube 5 is made from standard stainless hypodermic tubing. All materials to construct the invention are available from Small Parts Inc (www.smallparts.com). While the detailed description showed a specific embodiment of a clip with four barbs, it is obvious that the invention covers many other configurations of barbs, made from many materials including materials used to make absorbable sutures and other non-metallic clips. It is also obvious that the invention can be configured to be used on the outside rather than the inside wall of the body lumen by sliding a clip shown in FIG. 6-*b* on the outside of tube 5 and expanding it with the method shown in FIG. 7-*b*.

This is shown in FIGS. 9-*a* (closed position) and 9-*b* (open position). Tubes 4 and 5 slide over catheter 1 (but can be inside a larger catheter, not shown). Catheter 1 penetrates the wall of tissue 2 but tube 5 only reaches to the outside of tissue 2. Clip 3 is expanded by arms 16 actuated by taper 17 connected to tube 4. Many alternate expansion mechanisms are well known. After clip 3 is embedded in tissue 2, arms 16 are retracted and tubes 4 and 5 are withdrawn.

Figure 10:
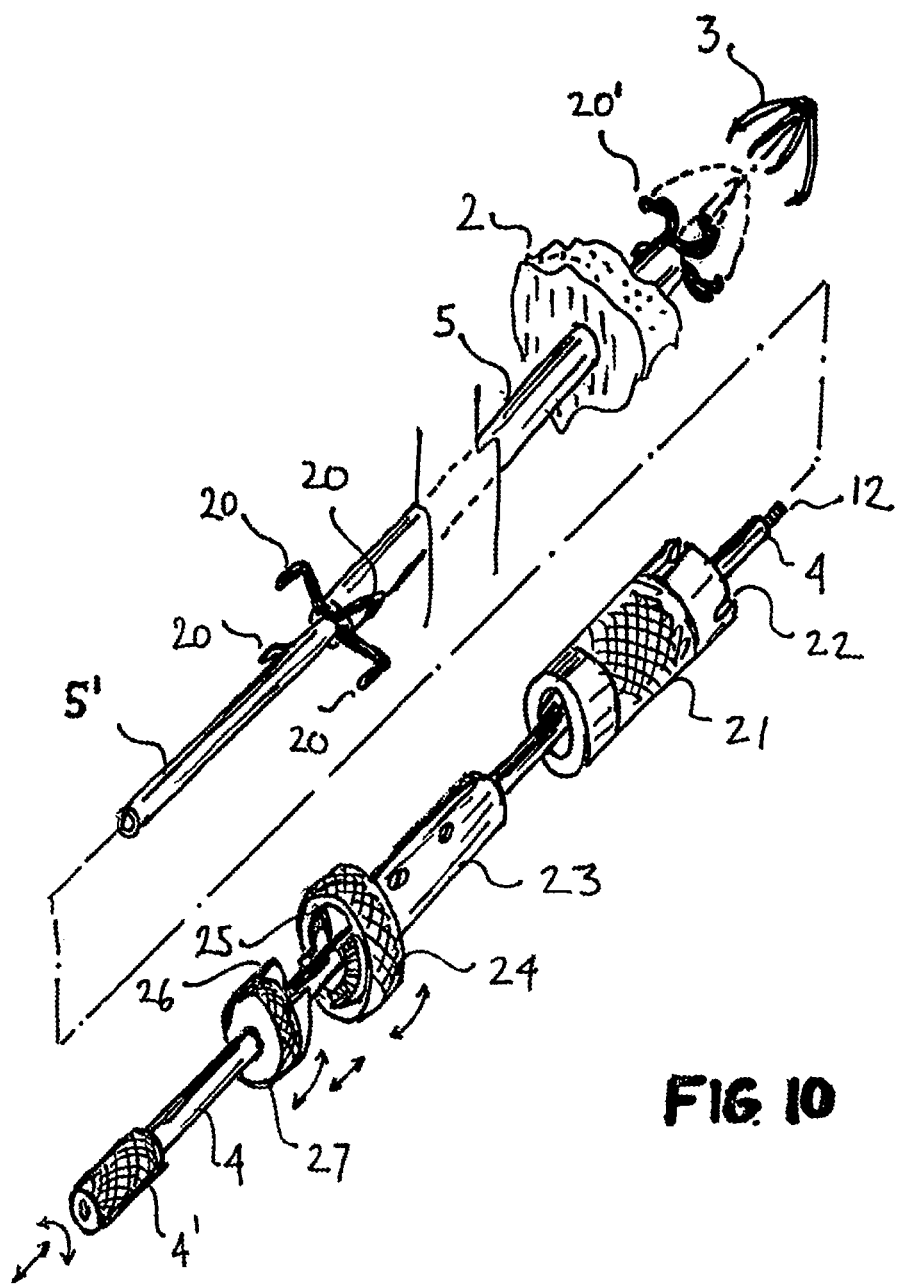
FIG. 10 is an "exploded" view of the preferred embodiment.

The preferred embodiment is shown in FIG. 10 as an "exploded" view. This embodiment used similar clips as the previous embodiments and a slightly more complex installation tool. The main additional advantages of this embodiment are:

ability to locate the tool within a lumen without use of monitoring such as x-ray or ultrasound.

ability to move the tool within the lumen without damage to the surrounding tissue.

To achieve these and further objectives, the sharp barbs of the clip are covered till ready to be embedded, and the tool provides a positive stop to locate the inside wall of the tissue. In FIG. 10 clip 3 is threaded onto the end of rod 4 via thread 12. A tube 5, made from extruded plastic or metal, has five holes running through it. Four of the holes are used for actuators 20 ending in arms 20'. The fifth hole is for rod 4. Actuators 20 can rotate inside tube 5 approximately 180 degrees, opening and closing clip 3. Actuators 20 engage in corresponding slots 22 in sleeve 21, which is free to rotate over shaft 23 which is clamped to extension 5' of tube 5. Rod 4 terminates in a section 4' resting on disc 27. By rotating disc 27 relative to shaft 23, disc 27 is moved axially away from shaft 23. This is achieved via inclined planes 25 and 26 but can be achieved by any one of the well known mechanisms converting rotary to linear motion such as threads, cams etc. When disc 27 is moved axially, it pulls rod 4 with it, causing clip 3 to slide over arms 20' and expand further. In operation, the tool is held by sleeve 21 and ring 24 is rotated to cause tube 5 to rotate. Since ends of actuators 20 are in slots 22, rotating tube 5 will cause actuators 20 to rotate and expand clip 3. After tool is in position, disc 27 is rotated to pull clip over arms 20' and embed barbs in tissue, followed by releasing the tool by turning end 4' of rod 4 to release tool from clip.

Figure 11:
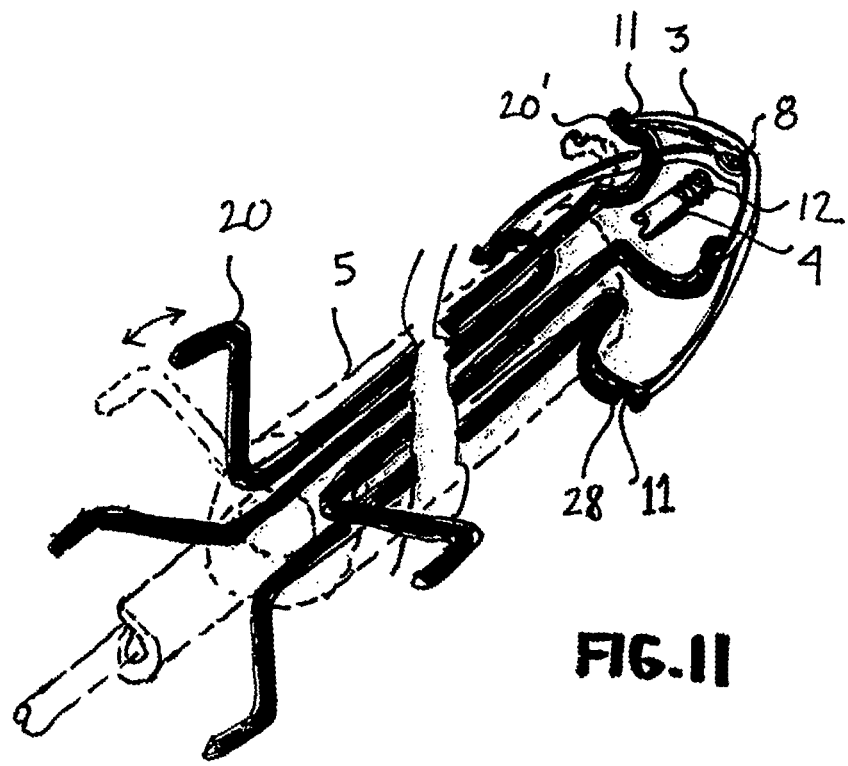
FIG. 11 is a "phantom" view of the actuation mechanism.

FIG. 11 is an enlarged view of both ends of actuators 20. At the end of each arm 20' there is a recess 28 into which barbed tip 11 of clip 3 fits. This provides a smooth outside surface till the barbs are exposed, and allows the tool to be moved inside a body lumen without damage. For example, when the device is used inside the heart, it is imperative to avoid snagging or damaging any one of the many cords attached to the valves. Clip 3 is attached to rod 4 via a thread 8 at center of clip.

Figure 12:
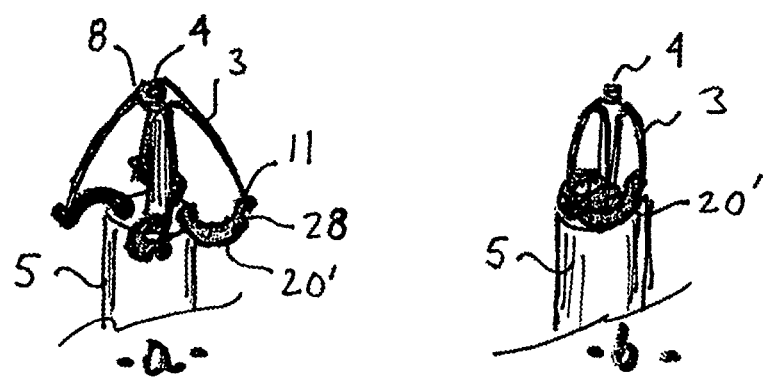
FIG. 12-a is a perspective view of the preferred embodiment in the fully open position.

FIG. 12-*a* is a close-up of the mounted clip in the expanded position while FIG. 12-*b* shows the refracted position. Each one of arms 20' is semi-circular, with an outside diameter approximately equal that of tube 5. The holes in tube 5 act as the pivot points for arms. At the outside edge of each arm 20' there is a recess 28 to hold tip 11 of clip 3. In the retracted position the arms 20' fold into a circle, overlapping each other. Clip 3 is still resting in recesses 28 of arms 20'. Clearly the semi-circles 20' are also bent towards thread 8, in order to allow them to fold partially over each other, in a manner resembling a four-start thread. The amount of axial forward bending is approximately equal to twice the diameter of the wire used to make actuator 20.

By the way of example, tube 4 is extruded plastic with a diameter of 4 to 8 mm. Actuators 20 are made of stainless steel wire having a diameter of 1.2-1.6 mm. Clip 3 is made of 0.3-0.5 mm thick Nitinol sheet or 0.6-0.9 Nitinol wire, as shown in FIG. 3.

FIG. 13 shows the steps in using the device. It is inserted via catheter 1 as shown in FIG. 13-*a*. Clip 3 is expanded by rotating ring 24. The expanded arms 20' provide a reference surface to locate the inner wall of tissue 2 without radiological means. Catheter 1 is pulled backwards till arms 20' stop at tissue 2, as shown in FIG. 13-*c*. Barbs of clip 3 are exposed by rotating disc 27 as shown in FIG. 13-*d*, and are embedded into tissue 2. In FIG. 13-*e*, ring 24 is further turned to fold the arms 20' into the refracted position while embedding clip 3 deeper in tissue 2, since rotating disc 24 both folds the arms and pulls on rod 4. After clip 3 is fully embedded in tissue rod 4 is turned to release clip 3 from tool 5. As with the other versions of the invention, the operation is reversible by re-attaching tool to clip. Note that ring 24 is turned to activate tool rather than bushing 21, since clip 3 needs to remain stationary relative to tissue 2 once it is embedded.

While the examples used an elastic clip, it is obvious that the invention can be practiced with a non-elastic deformable clip. By the way of example, the clip shown in FIG. 6 can be made of annealed stainless steel. The installation tools have to be slightly modified to be able to apply both tension and compression to the clip. Such a modification is shown in FIG. 7, wherein arm 16 has a bent tip 16' holding clip 3 from both sides. The clip can be deformed plastically from the shape shown in FIG. 6-*a* to the shape in FIG. 6-*b*, embedded in tissue 2 and deformed plastically back to the shape of FIG. 6-*a*. After that tool 5 is pushed forward to disengage from clip, arms 16 refracted and tool pulled out of catheter 1. The words "clip" and "barb" should be interpreted in a broad sense. Any part left behind in the tissue is considered a clip, regardless of actual shape or material. Any part of the clip used for attachment to the tissue is considered a "barb", regardless of shape, sharpness, material etc. By the way of example, in the context of this invention, an adhesive patch that can be placed over the hole from the inside and pull the hole to close is considered a clip and the adhesive is considered a barb.

The invention claimed is:

1. A medical apparatus to close a hole in cardiac tissue, the medical apparatus comprising:
   at least one tool; and
   a closure device comprising:
   a closed band,
   a central passage open at opposed ends thereof to selectively removably receive a portion of the at least one tool therethrough, and
   a plurality of barbs disposed radially about the central passage for attachment to the cardiac tissue,
   wherein the closure device is resiliently biased from a first configuration in which a radial size of the central passage has a first dimension toward a second configuration in which the radial size of the central passage has a second dimension, the second dimension smaller than the first dimension, and a portion of the closure device forming at least part of a periphery of the central passage, the at least part of the periphery of the central passage located radially inward from the plurality of barbs at least in the second configuration, and
   wherein the at least one tool includes a plurality of arms each with respective distal ends and proximate ends, the distal ends engaging the closed band of the closure device, the proximate ends pivotally coupled such that the distal ends are radially spaceable from one another between a retracted configuration and an expanded configuration to move the closure device from the second configuration to the first configuration.

2. The medical apparatus of claim 1, wherein the at least one tool cooperatively engages at least the part of the periphery of the central passage of the closure device to move the closure device between the second configuration and the first configuration.

3. The medical apparatus of claim 1 wherein the closure device is made of Nitinol.

4. The medical apparatus of claim 1 wherein the closure device comprises a plurality of lobes, a respective barb of the plurality of barbs extends from each lobe of the plurality of lobes.

5. The medical apparatus of claim 4 wherein the plurality of lobes surround the central passage.

6. The medical apparatus of claim 1 wherein, in each of the first configuration and the second configuration, each barb of the plurality of barbs extends generally parallel to a direction through the central passage along which the portion of the at least one tool is selectively removably receivable.

7. The medical apparatus of claim 1 wherein, in the first configuration, the closure device is in an expanded state and, in the second configuration, the closure device is in a relaxed state.

8. The medical apparatus of claim 7, wherein the at least one tool cooperatively engages at least the part of the periphery of the central passage of the closure device to move the closure device between the relaxed state and the expanded state.

9. The medical apparatus of claim 7 wherein, in at least the relaxed state, each barb of the plurality of barbs extends generally parallel to a direction through the central passage along which the portion of the at least one tool is selectively removably receivable.

10. The medical apparatus of claim 7 wherein each barb of the plurality of barbs is radially spaced outwardly from a longitudinal axis of the central passage by a respective first radial distance in the relaxed state and by a corresponding second radial distance in the expanded state, each first radial distance smaller than the corresponding second radial distance.

11. The medical apparatus of claim 7 wherein the at least part of the periphery of the central passage is located radially inward from the plurality of barbs by a first distance in the expanded state and by a second distance in the relaxed state, the first distance smaller than the second distance.

12. The medical apparatus of claim 1 wherein the at least part of the periphery of the central passage is located radially inward from the plurality of barbs by a first distance in the first configuration and by a second distance in the second configuration, the first distance smaller than the second distance.

13. The medical apparatus of claim 1 wherein, when mounted to the at least one tool for foreside implantation into the cardiac tissue, the barbs extend forwardly from a distal end of the at least one tool.

14. The medical apparatus of claim 1 wherein, when mounted to the at least one tool for blindside implantation into the cardiac tissue, the barbs extend rearwardly from a distal end of the at least one tool.

15. The medical apparatus of claim 1 wherein the closed band is made of Nitinol.

16. The medical apparatus of claim 1 wherein the closed band is tubular.

17. The medical apparatus of claim 16 wherein the closed band is multi-lobed.

18. The medical apparatus of claim 17 wherein each of the plurality of barbs are located at respective ones of the lobes.

19. The medical apparatus of claim 1, wherein the plurality of arms includes four arms, the distal ends of which are configured to engage the closed band of the closure device during implantation of the closure device.

20. The medical apparatus of claim 1 wherein the at least one tool includes a taper element mounted for translation along at least one catheter, and which physically engages the arms of the at least one tool to cause the arms to pivot between the retracted and the expanded configurations.

21. The medical apparatus of claim 20 wherein the taper element is at a distal end of a rod slideably received through a passage in a tube to which the arms are pivotally coupled, the tube received in a lumen of the at least one catheter.

22. The medical apparatus of claim 21 wherein the taper element engages the arms to pivotally expand the arms as the taper element moves away from the distal end with respect to the tube.

23. The medical apparatus of claim 20 wherein the taper element is at a distal end of a rod, the rod including a longitudinal passage that slideably receives the at least one catheter, the rod slideably received through a passage in a tube to which the arms are pivotally coupled.

24. The medical apparatus of claim 23 wherein the taper element engages the arms to pivotally expand the arms as the tube moves with respect to the rod.

25. The medical apparatus of claim 1, wherein the at least one tool cooperatively engages the closure device to move the closure device between a relaxed state and an expanded state.

26. The medical apparatus of claim 1 wherein the closed band comprises a laser cut structure.

27. The medical apparatus of claim 1
wherein, in the first configuration, tissue-penetrating-tips of the plurality of barbs are positioned to be arranged about the cardiac tissue that encompasses the hole just prior to embedding the tissue-penetrating-tips into the cardiac tissue, and
wherein the distal ends engage the closed band in an arrangement that avoids any contact with the tissue-penetrating tips of the plurality of barbs during a movement between the second configuration and the first configuration.

28. The medical apparatus of claim 1
wherein, in the first configuration, tissue-penetrating-tips of the plurality of barbs are positioned to be arranged about the cardiac tissue that encompasses the hole just prior to embedding the tissue-penetrating-tips into the cardiac tissue, and
wherein the distal ends engage the closed band in an arrangement that avoids any contact with the tissue-penetrating tips of the plurality of barbs during a movement of the portion of the at least one tool through the central passage in the second configuration.

29. The medical apparatus of claim 1 wherein the portion of the at least one tool, which is selectively removably receivable through the central passage, comprises a tissue-penetrating portion.

30. The medical apparatus of claim 29 wherein the portion of the at least one tool and the closure device are configured to close the hole in the cardiac tissue around the tissue penetrating portion while the tissue-penetrating portion is in a position configured to penetrate the cardiac tissue and while the at least one tool causes the peripheral portion to move between the second configuration and the first configuration.

31. The medical apparatus of claim 1 wherein the at least part of the periphery of the central passage is located radially inward from the plurality of barbs in the first configuration.

32. A medical apparatus to close a hole in cardiac tissue, the medical apparatus comprising:
at least one tool; and
a closure device comprising:
a central passage open at opposed ends thereof to selectively removably receive a portion of the at least one tool therethrough, and
a plurality of barbs disposed radially about the central passage for attachment to the cardiac tissue,
wherein the closure device is resiliently biased from a first configuration in which a radial size of the central passage has a first dimension toward a second configuration in which the radial size of the central passage has a second dimension, the second dimension smaller than the first dimension, and a portion of the closure device forming at least part of a periphery of the central passage, the at least part of the periphery of the central passage located radially inward from the plurality of barbs at least in the second configuration,
wherein the closure device comprises a plurality of lobes, a respective barb of the plurality of barbs extending from each lobe, and
wherein the at least one tool includes a plurality of arms each with respective distal ends and proximate ends, each of the distal ends respectively engaging one of the plurality of lobes, the proximate ends pivotally coupled such that the distal ends are radially spaceable from one another between a retracted configuration and an expanded configuration to move the closure device from the second configuration to the first configuration.

33. A medical apparatus to close holes in a cardiac tissue, comprising:
a closure device comprising a lobed band with a central passage open at opposed ends thereof, and a plurality of barbs disposed radially about the central passage and extending generally longitudinally from the lobed band for selective attachment to the cardiac tissue, the closure device resiliently biased from a first configuration in which a radial size of the central passage has a first dimension toward a second configuration in which the radial size of the central passage has a second dimension, the second dimension smaller than the first dimension; and
a tool having a plurality of arms each with respective distal ends and proximate ends, at least a portion of the arms are selectively removably receivable together through the central passage of the lobed band at least during implantation of the closure device, the proximate ends of the arms pivotally coupled such that the distal ends are radially spaceable from one another between a retracted configuration and an expanded configuration to move the closure device from the second configuration to the first configuration.

34. The medical apparatus of claim 33, further comprising:
a tube having a longitudinal passage, the arms pivotally coupled to the tube at the proximate ends thereof; and
a rod translatable to selectively engage the arms with a tapered element.

35. The medical apparatus of claim 33 wherein the rod is translatably received in the longitudinal passage of the tube.

36. The medical apparatus of claim 35 wherein the tube is receivable through a lumen of a catheter.

37. The medical apparatus of claim 35 wherein the rod has a passage sized to slideably receive a catheter.

38. The medical apparatus of claim 33 wherein the lobed band comprises a laser cut metal structure.

* * * * *